United States Patent
Liu et al.

(10) Patent No.: US 10,550,111 B2
(45) Date of Patent: Feb. 4, 2020

(54) PYRIMIDINE UREA COMPOUND CONTAINING ISOXAZOLINES AND USE THEREOF

(71) Applicant: SHENYANG SINOCHEM AGROCHEMICALS R&D CO., LTD, Liaoning (CN)

(72) Inventors: Changling Liu, Liaoning (CN); Jichun Yang, Liaoning (CN); Hongjuan Ma, Liaoning (CN); Qiao Wu, Liaoning (CN); Dongliang Cui, Liaoning (CN); Kecheng Yan, Liaoning (CN); Miao Li, Liaoning (CN)

(73) Assignee: SHENYANG SINOCHEM AGROCHEMICALS R&D CO., LTD., Shenyang, Liaoning (CN)

( * ) Notice: Subject to any disclaimer, the term of this patent is extended or adjusted under 35 U.S.C. 154(b) by 0 days.

(21) Appl. No.: 15/527,864

(22) PCT Filed: Dec. 14, 2015

(86) PCT No.: PCT/CN2015/097223
§ 371 (c)(1),
(2) Date: May 18, 2017

(87) PCT Pub. No.: WO2016/095768
PCT Pub. Date: Jun. 23, 2016

(65) Prior Publication Data
US 2018/0230139 A1 Aug. 16, 2018

(30) Foreign Application Priority Data
Dec. 16, 2014 (CN) .......................... 2014 1 0781642

(51) Int. Cl.
*A01N 43/80* (2006.01)
*C07D 413/10* (2006.01)
*C07D 413/14* (2006.01)

(52) U.S. Cl.
CPC .......... *C07D 413/10* (2013.01); *A01N 43/80* (2013.01); *C07D 413/14* (2013.01)

(58) Field of Classification Search
None
See application file for complete search history.

(56) References Cited

U.S. PATENT DOCUMENTS

| | | | |
|---|---|---|---|
| 5,336,663 A | 8/1994 | Wenger et al. | |
| 6,706,886 B2 * | 3/2004 | von Deyn | C07C 251/48 548/240 |
| 6,992,044 B1 | 1/2006 | Andree et al. | |
| 7,754,880 B2 | 7/2010 | Meazza et al. | |
| 9,078,442 B2 | 7/2015 | Willms et al. | |
| 9,585,392 B2 | 3/2017 | Kuhn et al. | |
| 2006/0223848 A1 | 10/2006 | Chang et al. | |
| 2007/0155738 A1 | 7/2007 | Steeneck et al. | |

FOREIGN PATENT DOCUMENTS

| | | |
|---|---|---|
| CN | 1061966 A | 6/1992 |
| CN | 100482648 C | 4/2009 |
| EP | 2044006 A1 | 4/2009 |
| WO | 2004/056785 A2 | 8/2004 |
| WO | 2006/090234 A1 | 8/2006 |
| WO | 2008/000438 A1 | 1/2008 |
| WO | 01/083459 A2 | 11/2011 |
| WO | 2012/130798 A1 | 10/2012 |
| WO | 2014/048827 A1 | 4/2014 |
| WO | 2014/048940 A2 | 4/2014 |

OTHER PUBLICATIONS

Patani, G.; et al. "Bioisosterism: A rational approach in Drug Design" Chemical Reviews, 1996, 96, 3147-3176. (Year: 1996).*
International Search Report dated Mar. 18, 2016 for PCT/CN2015/097223 (7 pages—Chinese and English).
Bambi-Nyanguile, Sylvie Mireille, et al. Synthesis and pharmacological evaluation of 2-aryloxy/arylamino-5-cyanobenzenesulfonylureas as novel thromboxane $A_2$ receptor antagonists. European Journal of Medicinal Chemistry, 2013, vol. 65, pp. 32-40.
Yeom, Chang-Eun, et al. Mild and Chemoselective Deacetylation Method Using a Catalytic Amount of Acetyl Chloride in Methanol. Synlett, 2005, No. 10, pp. 1527-1530.
García-Lago Ramón, et al. Synthesis of 2,4-dibromopyridine and 4,4'-dibromo-2,2'-bipyridine. Efficient usage in selective bromine-substitution under palladium-catalysis. Heterocycles, 2008, vol. 75, No. 1, pp. 57-64.

(Continued)

*Primary Examiner* — Erin E Hirt
(74) *Attorney, Agent, or Firm* — Smith, Gambrell & Russell, LLP

(57) ABSTRACT

The present invention relates to herbicide. Specifically to a kind of uracil compounds containing isoxazoline ring and the uses thereof. The present invention compounds have very good herbicidal activity, can effectively control weeds, such as *Echinochloa crusgalli*, *Setaria viridis*, *Cyperus difformis*, *Juncellus serotinus*, *Digitaria sangunalis*, *Arthraxon hispidus*, *Abutilon theophrasti*, *Zinnia elegans*, *Amaranthus retrofluxes*, *Portulaca oleracea*, *Xanthium sibiricum*, *Solanum nigrum*, *Cassia tora*, *Hibiscus trionum*, *Glycine soja*, an so on. They can effectively control weeds even at lower doses. The present invention compounds also safe to wheats, corns and rices, and can used as herbicides in agriculture fields.

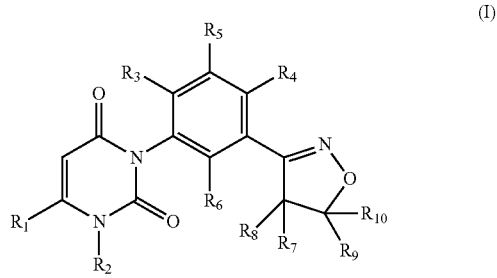

6 Claims, No Drawings

(56) References Cited

OTHER PUBLICATIONS

Hwang, In Taek, et al. 5-(2,6-Difluorobenzyl) oxymethyl-5-methyl-3-(3-mehtylthiophen-2-yl)-1,2-isoxazoline as a useful rice herbicide. Journal of Agricultural and Food Chemistry. 2005, vol. 53, pp. 8639-8643.

Chandrappa, S, et al. An Efficient Method for Aryl Nitro Reduction and Cleavage of Azo Compounds Using Iron Powder/Calcium Chloride. Synlett, 2010, No. 20, pp. 3019-3022.

Moreira Lima, L., et al. Bioisoterism: A useful Strategy for Molecular Modification and Drug Design. Current Medicinal Chemistry, 2005, vol. 12, pp. 23-49.

Koyanagi, T, et al. A New Phosporamidothioate Insecticide and Nematicide. Synthesis and Chemistry of Agrochemicals. American Chemical Society. 1991. Chapter 30, pp. 387-399.

Selby, T. P., et al. Broad Spectrum PPO-inhibiting N-Phenoxyphenyluracil Acetal Ester Herbicides. Discovery and Synthesis of Crop Protection Products. ACS Symposium Series. American Chemical Society. 2015. pp. 277-289.

First Office Action dated Sep. 19, 2018 in Chinese Patent Application No. 201580034859.7 (7 pages in Chinese with English translation).

Second Office Action dated Apr. 16, 2019 in Chinese Patent Application No. 201580034859.7 (9 pages in Chinese with English translation).

Written Opinion of the International Searching Authority dated Mar. 18, 2016 for International Patent Application No. PCT/CN2015/097223 (4 pages in Chinese with English translation).

International Preliminary Report on Patentability dated Jun. 20, 2017 for International Patent Application No. PCT/CN2015/097223 (5 pages in Chinese with English translation).

\* cited by examiner

PYRIMIDINE UREA COMPOUND CONTAINING ISOXAZOLINES AND USE THEREOF

FIELD OF THE INVENTION

The present invention relates to herbicide. Specifically to a kind of uracil compounds containing isoxazoline ring and the uses thereof.

BACKGROUND OF THE INVENTION

The research of uracil derivatives as herbicides began in the 1960s and peaked in the 1990s. Although the development of uracil herbicides were seldom reported, some patents of uracil derivatives were often disclosed. Isagro Ricerca disclosed the following general formula in WO2004056785. However, the herbicidal properties of these known compounds are not always entirely satisfactory.

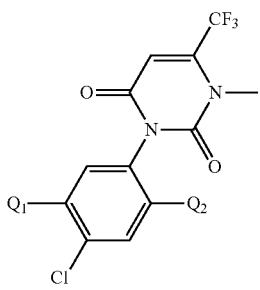

Wherein: $Q_1$ was 5-membered heterocycle such as oxazolyl, thiazolyl, benzoxazolyl, benzothienyl, benzothiazolyl, etc. $Q_2$ was F or H.

Even though some similarity can be observed between published compounds in the prior art and the present invention compounds, the compounds having the structure of general formula (I) were different significantly from those in prior art, and have good herbicidal activity as well.

SUMMARY OF THE INVENTION

In order to discover and develop new herbicides for solving the increasing problem of resistance, the present invention provides a kind of uracil compounds containing isoxazoline ring and the uses thereof.

In order to achieve the above object, technical solution of the present invention is as follows:

The present invention provides a kind of uracil compounds containing isoxazoline ring having general formula (I):

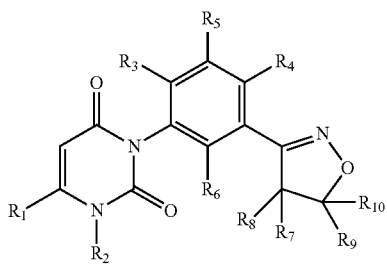

(I)

Wherein:

$R_1$, $R_2$ are selected from $C_1$-$C_6$alkyl or $C_1$-$C_6$haloalkyl;

$R_3$, $R_4$, $R_5$, $R_6$ are selected from H, halogen, $C_1$-$C_6$alkyl, $C_1$-$C_6$alkoxy, $C_1$-$C_6$haloalkoxy, $C_1$-$C_6$alkylthio or $C_1$-$C_6$alkylsulfonyl;

$R_7$, $R_8$ are selected from H, CN, $C_1$-$C_6$alkyl, $CO_2R_{11}$, $CH_2OR_{12}$, phenyl, or phenyl substituted with 1-4 substitutents selected from halogen, CN, $NO_2$, $C_1$-$C_8$alkyl, $C_1$-$C_8$haloalkyl, $C_1$-$C_8$alkoxy, $C_1$-$C_8$haloalkoxy, $C_1$-$C_8$alkoxycarbonyl, $C_1$-$C_8$alkylthio or $C_1$-$C_8$alkylsulfonyl;

$R_9$, $R_{10}$ are selected from H, CN, $C_1$-$C_6$alkyl, $C_1$-$C_6$haloalkyl, $CO_2R_{11}$, $CH_2OR_{12}$, $CH_2NR_{13}R_{14}$, $CONR_{13}R_{14}$, phenyl, or phenyl substituted with 1-4 substitutents selected from halogen, CN, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylthio or $C_1$-$C_4$alkylsulfonyl;

$R_{11}$ is selected from H, $C_1$-$C_6$alkyl, $C_1$-$C_6$haloalkyl, $C_3$-$C_6$alkenyl, $C_3$-$C_6$alkynyl, $C_1$-$C_6$alkoxy$C_1$-$C_6$alkyl, $C_1$-$C_6$alkoxycarbonyl$C_2$-$C_4$alkyl, unsubstituted or substituted following groups: benzyl, furanmethyl, thiazolemethyl, tetrahydrofuranmethyl or pyridinemethyl, which is mutually independently optionally substituted with 1-4 substitutents selected from halogen, CN, $NO_2$, $C_1$-$C_8$alkyl, $C_1$-$C_8$haloalkyl, $C_1$-$C_8$alkoxy, $C_1$-$C_8$haloalkoxy, $C_1$-$C_8$alkoxycarbonyl, $C_1$-$C_8$alkylthio or $C_1$-$C_8$alkylsufonyl;

$R_{12}$ is selected from H, $C_1$-$C_6$alkyl, $C_1$-$C_6$haloalkyl, $C_1$-$C_6$alkoxycarbonyl, $C_1$-$C_6$alkylcarbonyl, $C_1$-$C_6$haloalkylcarbonyl, $C_3$-$C_6$cycloalkylcarbonyl, $C_3$-$C_6$halocycloalkylcarbonyl, $C_1$-$C_6$alkylsulfonyl, $C_1$-$C_6$haloalkylsulfonyl, $C_1$-$C_6$alkylaminosulfonyl, di($C_1$-$C_6$)alkylaminosulfonyl, $C_1$-$C_6$alkylaminocarbonyl, di($C_1$-$C_6$)alkylaminocarbonyl, di($C_1$-$C_6$)alkylaminothiocarbonyl, $C_1$-$C_6$alkylthio$C_2$-$C_6$alkylcarbonyl. $R_{12}$ is also selected from unsubstituted or substituted following groups: phenyl, phenyl$C_1$-$C_2$alkyl, phenyl$C_2$-$C_4$alkenyl, phenylcarbonyl, phenyl$C_1$-$C_2$alkylcarbonyl, phenoxy$C_1$-$C_2$alkylcarbonyl, phenyl$C_2$-$C_4$alkenylcarbonyl, heteroaryl, heteroaryl$C_1$-$C_2$alkyl or heteroarylcarbonyl, which is mutually independently optionally substituted with 1-4 substituents selected from halogen, CN, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl; $C_1$-$C_4$alkylthio, $C_1$-$C_4$alkylsulfonyl, or phenoxy substituted with 1-4 substitutents selected from halogen, CN, $NO_2$, $C_1$-$C_4$alkyl, $C_1$-$C_4$haloalkyl, $C_1$-$C_4$alkoxy or $C_1$-$C_4$haloalkoxy;

$R_{13}$, $R_{14}$ are selected from H, $C_1$-$C_6$alkyl, $C_1$-$C_6$haloalkyl, $C_1$-$C_6$alkoxycarbonyl$C_1$-$C_6$alkyl; or $R_{13}$ joined together with $R_{14}$ through N to form five or six membered ring.

The preferred compounds of general formula (I) of this invention are:

$R_1$ is selected from $C_1$-$C_4$haloalkyl;
$R_2$ is selected from $C_1$-$C_4$alkyl or $C_1$-$C_4$haloalkyl;
$R_3$, $R_4$, $R_5$, $R_6$ are selected from H, halogen, $C_1$-$C_6$alkyl or $C_1$-$C_6$alkoxy;
$R_7$ is selected from H or $C_1$-$C_6$alkyl;
$R_8$ is selected from H, $C_1$-$C_6$alkyl, $CO_2R_{11}$ or $CH_2OR_{12}$;
$R_9$ is selected from H, CN, $C_1$-$C_6$alkyl, $C_1$-$C_6$haloalky, $CO_2R_{11}$, $CH_2OR_{12}$, $CH_2NR_{13}R_{14}$ or $CONR_{13}R_{14}$;
$R_{10}$ is selected from H, $C_1$-$C_6$alkyl, $C_1$-$C_6$haloalkyl, phenyl, or phenyl substituted with 1-4 substitutents selected from halogen, CN, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylthio or $C_1$-$C_4$alkylsulfonyl;

$R_{11}$ is selected from H, $C_1$-$C_6$alkyl, $C_1$-$C_6$haloalkyl, $C_3$-$C_4$alkenyl, $C_3$-$C_4$alkynyl, $C_1$-$C_4$alkoxy$C_1$-$C_4$alkyl, $C_1$-$C_4$alkoxycarbonyl$C_2$-$C_3$alkyl, unsubstituted or substituted following groups: benzyl, furanmethyl, or tetrahydrofuranmethyl, which is mutually independently optionally substituted with 1-4 substitutents selected from halogen, CN, $NO_2$, $C_1$-$C_6$alkyl or $C_1$-$C_6$haloalkyl;

$R_{12}$ is selected from H, $C_1$-$C_6$alkyl, $C_1$-$C_6$haloalkyl, $C_1$-$C_6$alkoxycarbonyl, $C_1$-$C_6$alkylcarbonyl, $C_1$-$C_6$haloalkylcarbonyl, $C_3$-$C_6$cycloalkylcarbonyl, $C_3$-$C_6$halocycloalkylcarbonyl, $C_1$-$C_6$alkylsulfonyl, $C_1$-$C_6$haloalkylsulfonyl, $C_1$-$C_6$alkylaminosulfonyl, di($C_1$-$C_6$)alkylaminosulfonyl, $C_1$-$C_6$alkylaminocarbonyl, di($C_1$-$C_6$)alkylaminocarbonyl, di($C_1$-$C_6$)alkylaminothiocarbonyl, $C_1$-$C_6$alkylthio$C_2$-$C_6$alkylcarbonyl. $R_{12}$ is also selected from unsubstituted or substituted following groups: phenyl$C_1$-$C_2$alkyl, phenylcarbonyl, phenyl$C_1$-$C_2$alkylcarbonyl, phenoxy$C_1$-$C_2$alkylcarbonyl, phenyl$C_2$-$C_4$alkenylcarbonyl, thiophenylcarbonyl, pyrazolcarbonyl or quinolinecarbonyl, which is mutually independently optionally substituted with 1-4 substitutents selected from halogen, CN, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylthio, $C_1$-$C_4$alkylsulfonyl, or phenoxy substituted with 1-4 substitutents selected from halogen, CN, $NO_2$, $C_1$-$C_4$alkyl, $C_1$-$C_4$haloalkyl, $C_1$-$C_4$alkoxy or $C_1$-$C_4$haloalkoxy;

$R_{13}$, $R_{14}$ are selected from H, $C_1$-$C_4$alkyl, $C_1$-$C_4$haloalkyl or $C_1$-$C_4$alkoxycarbonyl$C_1$-$C_4$alkyl; or $R_{13}$ joined together with $R_{14}$ through N to form five or six membered ring.

Furthermore, the preferred compounds of general formula (I) of this invention are:

$R_1$ is $CF_3$;
$R_2$ is $CH_3$;
$R_3$, $R_4$, $R_5$, $R_6$ are selected from H, halogen or $C_1$-$C_4$alkyl;
$R_7$ is selected from H or $C_1$-$C_4$alkyl;
$R_8$ is selected from H, $C_1$-$C_4$alkyl, $CO_2R_{11}$ or $CH_2OR_{12}$;
$R_9$ is selected from H, CN, $C_1$-$C_4$alkyl, $C_1$-$C_4$haloalkyl, $CO_2R_{11}$, $CH_2OR_{12}$, $CH_2NR_{13}R_{14}$ or $CONR_{13}R_{14}$;
$R_{10}$ is selected from H, $C_1$-$C_4$alkyl, $C_1$-$C_4$haloalkyl, phenyl, or phenyl substituted with 1-4 substitutents selected, from halogen, CN, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylthio or $C_1$-$C_4$alkylsulfonyl;
$R_{11}$ is selected from H, $C_1$-$C_4$alkyl, $C_1$-$C_4$haloalkyl, $C_3$-$C_4$alkenyl, $C_3$-$C_4$alkynyl, $C_1$-$C_4$alkoxy$C_1$-$C_4$alkyl, $C_1$-$C_4$alkoxycarbonyl$C_2$-$C_3$alkyl, unsubstituted or substituted following groups; benzyl, furanmethyl, or tetrahydrofuranmethyl, which is mutually independently optionally substituted with 1-4 substitutents selected from halogen, CN, $NO_2$, $C_1$-$C_4$alkyl or $C_1$-$C_4$haloalkyl;

$R_{12}$ is selected from H, $C_1$-$C_4$alkyl, $C_1$-$C_4$haloalkyl, $C_1$-$C_4$alkoxycarbonyl, $C_1$-$C_4$alkylcarbonyl, $C_1$-$C_4$haloalkylcarbonyl, $C_3$-$C_6$cycloalkylcarbonyl, $C_3$-$C_6$halocycloalkylcarbonyl, $C_1$-$C_4$alkylsulfonyl, $C_1$-$C_4$haloalkylsulfonyl, $C_1$-$C_3$alkylaminosulfonyl, di($C_1$-$C_3$)alkylaminosulfonyl, $C_1$-$C_3$alkylaminocarbonyl, di($C_1$-$C_3$)alkylaminocarbonyl, di($C_1$-$C_3$alkylaminothiocarbonyl, $C_1$-$C_2$alkylthio$C_2$-$C_4$alkylcarbonyl. $R_{12}$ is also selected from unsubstituted or substituted following groups; phenyl$C_1$-$C_2$alkyl, phenylcarbonyl, phenyl$C_1$-$C_2$alkylcarbonyl, phenoxy$C_1$-$C_2$alkylcarbonyl, phenyl$C_2$-$C_4$alkenylcarbonyl, thiophenylcarbonyl, pyrazolcarbonyl or quinolinecarbonyl, which is mutually independently optionally substituted with 1-4 substitutents selected from halogen, CN, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylthio, $C_1$-$C_4$alkylsulfonyl, or phenoxy substituted with 1-4 substitutents selected from halogen, CN, $NO_2$, $C_1$-$C_4$alkyl, $C_1$-$C_4$haloalkyl, $C_1$-$C_4$alkoxy or $C_1$-$C_4$haloalkoxy;

$R_{13}$, $R_{14}$ are selected from H, $C_1$-$C_4$alkyl, $C_1$-$C_4$haloalkyl or $C_1$-$C_4$alkoxycarbonyl$C_1$-$C_4$alkyl; or $R_{13}$ joined together with $R_{14}$ through N to form five or six membered ring.

Even more preferred compounds of formula (I) of this invention are:

$R_1$ is $CF_3$;
$R_2$ is $CH_3$;
$R_3$, $R_4$, $R_5$, $R_6$ are selected from H, F, Cl or $CH_3$;
$R_7$ is selected from H or $CH_3$;
$R_8$ is selected from H, $CH_3$, $CO_2R_{11}$ or $CH_2OR_{12}$;
$R_9$ is selected from H, CN, $CH_3$, $C_2H_5$, $CH_2Cl$, $CH_2Br$, $CO_2R_{11}$, $CH_2OR_{12}$, $CH_2NR_{13}R_{14}$ or $CONR_{13}R_{14}$;
$R_{10}$ is selected from H, $C_1$-$C_4$alkyl, $C_1$-$C_4$haloalkyl, phenyl, or phenyl substituted with 1-4 substituents selected from halogen, CN, $NO_2$, $C_1$-$C_4$alkyl, $C_1$-$C_4$haloalkyl, $C_1$-$C_4$alkoxy or $C_1$-$C_4$haloalkoxy;
$R_{11}$ is selected from H, $C_1$-$C_4$alkyl, $C_1$-$C_4$haloalkyl, allyl, propargyl, $C_1$-$C_3$alkoxy$C_1$-$C_3$alkyl, $C_1$-$C_4$alkoxycarbonyl$C_2$-$C_3$alkyl, unsubstituted or substituted following groups: benzyl, furanmethyl, or tetrahydrofuranmethyl, or above benzyl, furanmethyl and tetrahydrofuranmethyl which is mutually independently optionally substituted with 1-4 substituents selected from halogen, CN, $NO_2$ or $C_1$-$C_4$alkyl;
$R_{12}$ is selected from H, $C_1$-$C_4$alkyl, $C_1$-$C_4$haloalkyl, $C_1$-$C_4$alkoxycarbonyl, $C_1$-$C_4$alkylcarbonyl, $C_1$-$C_4$haloalkylcarbonyl, $C_3$-$C_6$cycloalkylcarbonyl, $C_1$-$C_4$alkylsulfonyl, $C_1$-$C_4$haloalkylsulfonyl, di($C_1$-$C_3$)alkylaminosulfonyl, $C_1$-$C_3$alkylaminocarbonyl, di($C_1$-$C_3$)alkylaminocarbonyl, di($C_1$-$C_3$)alkylaminothiocarbonyl, $C_1$-$C_2$alkylthio$C_2$-$C_4$alkylcarbonyl. $R_{12}$ is also selected from unsubstituted or substituted following groups: phenylcarbonyl, phenyl$C_1$-$C_2$alkylcarbonyl, phenoxy$C_1$-$C_2$alkylcarbonyl, thiophenylcarbonyl, pyrazolcarbonyl or quinolinecarbonyl, which is mutually independently optionally substituted with 1-4 substituents selected from halogen, CN, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylthio, $C_1$-$C_4$alkylsulfonyl or 2-chloro-4-trifluoromethyl-phenoxy;
$R_{13}$, $R_{14}$ are selected from H, $C_1$-$C_4$alkyl, $C_1$-$C_4$haloalkyl or $C_1$-$C_4$alkoxycarbonyl$C_1$-$C_4$alkyl; or $R_{13}$ joined together with $R_{14}$ through N to form five or six membered ring.

Even more compounds of general formula (I) of the invention are;

$R_1$ is $CF_3$;
$R_2$ is $CH_3$;
$R_3$, $R_4$ are selected from H, F, Cl or $CH_3$;
$R_5$, $R_6$ are H;
$R_7$ is selected from H or $CH_3$;
$R_8$ is selected from H, $CH_3$, $CO_2R_{11}$ or $CH_2OR_2$;
$R_9$ is selected from H, CN, $CH_3$, $C_2H_5$, $CH_2Cl$, $CH_2Br$, $CO_2R_{11}$, $CH_2OR_{12}$ or $CONR_{13}R_{14}$;
$R_8$, $R_9$ are not selected from $CO_2R_{11}$ or $CH_2OR_{12}$ at the same;
$R_{10}$ is selected from H, $CH_3$, $C_2H_5$, $CF_3$, $CHF_2$, phenyl, or phenyl substituted with 1-4 substituents selected from halogen, CN, $NO_2$, $C_1$-$C_4$alkyl, $C_1$-$C_4$haloalkyl, $C_1$-$C_4$alkoxy or $C_1$-$C_4$haloalkoxy;
$R_{11}$ is selected from H, $CH_3$, $C_2H_5$, $CH_3CH_2CH_2$, $CH_3CH_2CH_2CH_2$, $(CH_3)_2CH$, $(CH_3)_2CHCH_2$, $(CH_3)_3C$, $CF_3CH_2$, allyl, propargyl, $CH_3OCH_2CH_2$, $C_2H_5OCH_2CH_2$, $CH_3CO_2CH_2CH_2$ or tetrahydrofuranmethyl;
$R_{12}$ is selected from H, $C_1$-$C_4$alkoxycarbonyl, $C_1$-$C_4$alkylcarbonyl, $C_1$-$C_4$haloalkylcarbonyl, $C_3$-$C_6$cycloalkylcarbonyl, $C_1$-$C_4$alkylsulfonyl, $C_1$-$C_4$haloalkylsulfonyl, di($C_1$-$C_2$)alkylaminosulfonyl, $C_1$-$C_2$alkylaminocarbonyl, di($C_1$-$C_3$)alkylaminocarbonyl, di($C_1$-$C_2$)alkylaminothiocarbonyl, $C_1$-$C_2$alkylthio$C_2$-$C_4$alkylcarbonyl. $R_{12}$ is also selected from unsubstituted or substituted following groups: phenylcarbonyl, phenyl$C_1$-$C_2$alkylcarbonyl, phenoxy$C_1$-$C_2$alkylcarbonyl, thiophenylcarbonyl or quinolinecarbonyl, which is mutually independently optionally substituted with 1-4 substitutents selected from halogen, CN, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylthio, $C_1$-$C_4$alkylsulfonyl or 2-chloro-4-trifluoromethyl-phenoxy;

$R_{13}$ is selected from H, $C_1$-$C_4$alkyl or $C_1$-$C_4$haloalkyl;

$R_{14}$ is selected from H, $C_1$-$C_4$alkyl or $C_1$-$C_4$alkoxycarbonyl$C_1$-$C_4$alkyl;

or $R_{13}$ joined together with $R_{14}$ through N to form five or six membered ring.

Even more compounds of general formula (I) of the invention are:

$R_1$ is $CF_3$;

$R_2$ is $CH_3$;

$R_3$, $R_4$ are selected from H, F or Cl;

$R_5$, $R_6$, are H;

$R_7$ is selected from H or $CH_3$:

$R_8$ is selected from H, $CH_3$, $CO_2R_{11}$ or $CH_2OR_{12}$;

$R_9$ is selected from H, CN, $CH_3$, $C_2H_5$, $CH_2Cl$, $CH_2Br$, $CO_2R_{11}$, $CH_2OR_{12}$ or $CONR_{13}R_{14}$;

$R_8$, $R_9$ are not selected from $CO_2R_{11}$ or $CH_2OR_{12}$ at the same;

$R_{10}$ is selected from H, $CH_3$ or $C_2H_5$;

$R_{11}$ is selected from H, $CH_3$, $C_2H_5$, $CH_3CH_2CH_2$, $CH_3CH_2CH_2CH_2$, $(CH_3)_2CH$, $(CH_3)_2CHCH_2$, $(CH_3)_3C$, $CF_3CH_2$, allyl, propargyl, $CH_3OCH_2CH_2$, $CH_2H_5OCH_2CH_2$, $CH_3CO_2CH_2CH_2$ or tetrahydrofuranmethyl;

$R_{12}$ is selected from H, $C_1$-$C_4$alkylcarbonyl, $C_1$-$C_4$haloalkylcarbonyl, $C_3$-$C_6$cycloalkylcarbonyl, $C_1$-$C_4$alkylsulfonyl, $C_1$-$C_4$haloalkylsulfonyl, di($C_1$-$C_2$)alkylaminosulfonyl, di($C_1$-$C_3$)alkylaminocarbonyl, di($C_1$-$C_2$)alkylaminothiocarbonyl, $C_1$-$C_2$alkylthio$C_2$-$C_4$alkylcarbonyl, phenyl$C_1$-$C_2$alkylcarbonyl, 2-methyl-4-chlorophenoxyacetyl, 2,4-dichlorophenoxyacetyl or thiophenylcarbonyl;

$R_{12}$ is also selected from

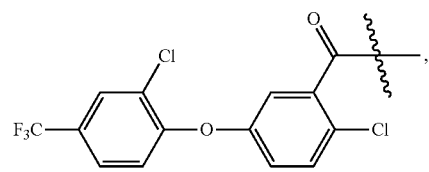

,

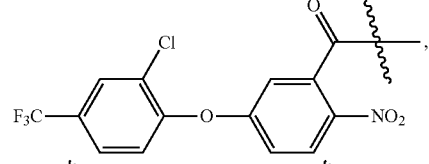

,

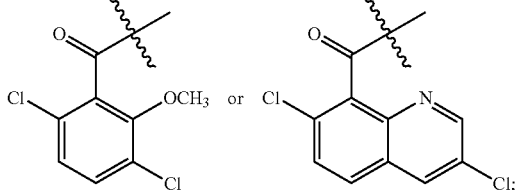

;

$R_{13}$ is selected from H, $C_1$-$C_4$alkyl or $C_1$-$C_4$haloalkyl;

$R_{14}$ is selected from H, $C_1$-$C_4$alkyl or $C_1$-$C_4$alkoxycarbonyl$C_1$-$C_4$alkyl;

or $R_{13}$ joined together with $R_{14}$ through N to form

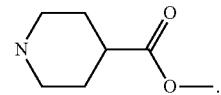

.

The most preferred compounds of general formula (I) of the invention are:

$R_1$ is $CF_3$;

$R_2$ is $CH_3$;

$R_3$, $R_4$ are selected from H, F or Cl;

$R_5$, $R_6$, $R_7$, $R_8$ are H;

$R_9$ is selected from H, CN, $CH_3$, $C_2H_5$, $CH_2Cl$, $CH_2Br$, $CO_2R_{11}$, $CH_2OR_{12}$ or $CONR_{13}R_{14}$;

$R_{10}$ is selected from H, $CH_3$ or $C_2H_5$;

$R_{11}$ is selected from H, $CH_3$, $C_2H_5$, $CH_3CH_2CH_2$, $CH_3CH_2CH_2CH_2$, $(CH_3)_2CH$, $(CH_3)_2CHCH_2$, $(CH_3)_3C$, $CF_3CH_2$, allyl, propargyl, $CH_3OCH_2CH_2$, $C_2H_5OCH_2CH_2$, $CH_3CO_2CH_2CH_2$ or tetrahydrofuranmethyl;

$R_{12}$ is selected from H, $C_1$-$C_4$alkylcarbonyl, $C_1$-$C_4$haloalkylcarbonyl, cyclopropylcarbonyl, $C_1$-$C_4$alkylsulfonyl, $C_1$-$C_4$haloalkylsulfonyl, di($C_1$-$C_2$)alkylaminosulfonyl, di($C_1$-$C_3$)alkylaminocarbonyl, di($C_1$-$C_2$)alkylaminothiocarbonyl, $C_1$-$C_2$alkylthio$C_2$-$C_4$alkylcarbonyl, phenyl$C_1$-$C_2$alkylcarbonyl, 2-methyl-4-chlorophenoxyacetyl, 2,4-dichlorophenoxyacetyl or thiophenylcarbonyl;

$R_{12}$ is also selected from

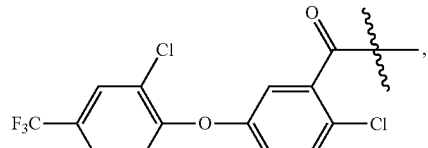

,

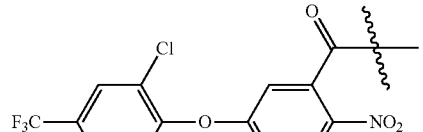

,

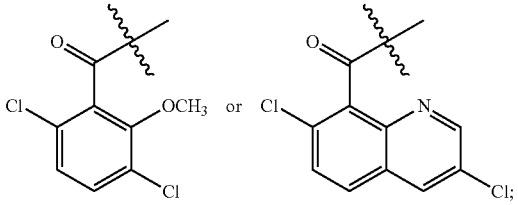

;

$R_{13}$ is selected from H, $CH_3$, $C_2H_5$, $(CH_3)_2CH$, $CH_3CH_2CH_2$, $CH_3CH_2CH_2CH_2$, $(CH_3)_3C$, $CF_3CH_2$, $CHF_2CH_2$, $CH_2CH_2Cl$, $CH_2CH_2CH_2Cl$ or $(CH_3)CHCH_2Cl$;

$R_{14}$ is selected from H, $CH_3$, $C_2H_5$, $(CH_3)_2CH$, $CH_3CH_2CH_2$, $CH_3CH_2CH_2CH_2$, $(CH_3)_3C$, or $C_1$-$C_4$alkoxycarbonyl$C_1$-$C_4$alkyl;

or R$_{13}$ joined together with R$_{14}$ through N to form

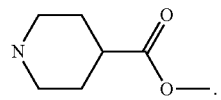

The terms used above to definite the compounds having general formula (I) represent substitutes as follow:

Halogen or halo is fluorine, chlorine, bromine or iodine. The alkyl is to be understood as meaning straight or branched chain alkyl, such as methyl, ethyl, n-propyl, i-propyl, n-butyl, or the different butyl, pentyl or hexyl isomers. Cycloalkyl is monocyclic saturated hydrocarbonyl groups having 3 to 8 carbon atoms, such as cyclopropyl, cyclobutyl, cyclopentyl or cycloheyl etc. The haloalkyl stands for straight or branched chain alkyl, in which hydrogen atoms can be all or partly substituted with halogen, such as chloromethyl, dichloromethyl, trichloromethyl, fluoromethyl, difluoromethyl, trifluoromethyl or heptafluoroisopropyl, etc. The alkoxy refers to straight or branched chain alkyl, which is linked to the structure by oxygen atom, such as OCH$_3$, OC$_2$H$_5$ or OC(CH$_3$)$_3$. The haloalkoxy refers to straight or branched chain alkoxy, in which hydrogen atoms may be all or partly substituted with halogen, such as chloromethoxy, dichloromethoxy, trichloromethoxy, fluoromethoxy, difluoromethoxy, trifluoromethoxy, chlorofluoromethoxy, trifluoroethoxy, etc. The alkylthio refers to straight or branched chain alkyl, which is linked to the structure by sulfur atom. The haloalkylthio refers to straight or branched chain alkylthio, in which hydrogen atoms may be all or partly substituted with halogen, such as chloromethylthio, dichloromethylthio, trichloromethylthio, fluoromethylthio, difluoromethylthio, trifluoromethylthio, chlorofluoromethylthio, etc. The alkenyl refers to straight or branched chain alkenyl, such as ethenyl, 1-propenyl, 2-propenyl and different isomer of butenyl, pentenyl and hexenyl. Alkenyl also includes polyene, such as propa-1,2-dienyl and hexa-2,4-dienyl. The alkylsulfonyl refers to straight or branched chain alkyl, which is linked to the structure by sulfuryl, such as CH$_3$SO$_2$. The haloalkylsulfonyl refers to straight or branched chain alkylsulfonyl, in which hydrogen atom may be all or partly substituted with halogen. The alkoxycarbonyl refers to straight or branched chain alkoxy, which is linked to the structure by carbonyl(—CO—), such as CH$_3$OCO or CH$_3$CH$_2$OCO—. The alkoxyalkyl is alkyl-O-alkyl-, such as CH$_3$OCH$_2$—. The alkylcarbonyloxyalkoxycarbonyl is alkyl-CO—O-alkyl-OCO—, such as CH$_3$COOCH$_2$OCO—, CH$_3$COOCH$_2$CH$_2$OCO— or C$_2$H$_5$COOCH$_2$CH$_2$OCO—. The alkylcarbonyl refers to straight or branched chain alkyl, which is linked to the structure by carbonyl(—CO—), such as CH$_3$CO— or CH$_3$CH$_2$CO—. The haloalkylcarbonyl refers to straight or branched chain alkylcarbonyl, in which hydrogen atom may be all or partyl substituted with halogen, such as CF$_3$CO— or CF$_2$HCO—. The cycloalkylcarbonyl refers to cycloalkyl linked to the structure by carbonyl(—CO—), such as cyclopropylcarbonyl or cyclohexylcarbonyl. The halocycloalkylcarbonyl refers to cycloalkyl linked to the structure by carbonyl(—CO—), such as 1-chlorocyclopropylcarbonyl. The alkylaminosulfonyl is alkyl-NH—SO$_2$—, such as CH$_3$NHSO$_2$— or C$_2$H$_5$NHSO$_2$—. The dialkylaminosulfonyl is dialkyl-NH—SO$_2$—, such as (CH$_3$)$_2$NSO$_2$— or (C$_2$H$_5$)$_2$NSO$_2$—. The alkylaminocarbonyl is alkyl-NH—CO—, such as CH$_3$NHCO— or C$_2$H$_5$NHCO—. The dialkylaminocarbonyl is dialkyl-NH—CO—, such as (CH$_3$)$_2$NCO— or (C$_2$H$_5$)$_2$NCO—. The dialkylaminothiocarbonyl is dialkyl-N—CS—, such as (CH$_3$)$_2$NCS— or (C$_2$H$_5$)$_2$NCS—. The alkylthioalkylcarbonyl is alkyl-S-alkyl-CO, such as CH$_3$SCH$_2$CO or CH$_3$SCH$_2$CH$_2$CO. The heteroaryl stands for five member ring or six member ring containing one or more N, O, S hetero atoms. Such as furyl, pyrazolyl, thiazolyl, pyridinyl, pyrimidinyl, pyridazinyl, triazinyl or quinoxalinyl etc. Furanmethyl, thiazolemethyl, tetrahydrofuranmethyl and pyridinemethyl can be as

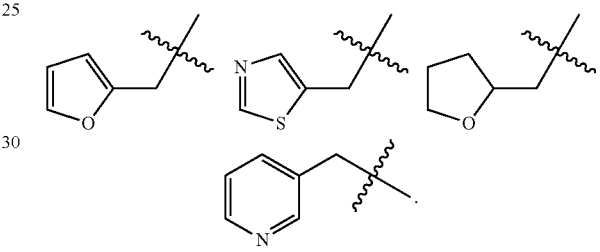

The present invention is also explained by the following compounds listed in Table 1, but without being restricted thereby. In formula (I), R$_1$—CF$_3$, R$_2$=CH$_3$, R$_5$, R$_6$=H, R$_3$, R$_4$, R$_7$, R$_8$, R$_9$, R$_{10}$ are listed in following Table 1.

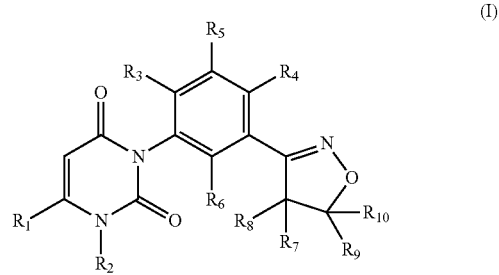

TABLE 1

| No. | R$_3$ | R$_4$ | R$_7$ | R$_8$ | R$_9$ | R$_{10}$ |
|---|---|---|---|---|---|---|
| 1 | F | Cl | H | H | CH$_3$ | CH$_3$ |
| 2 | F | Cl | H | H | C$_2$H$_5$ | CH$_3$ |
| 3 | F | Cl | H | H | cyclo-C$_3$H$_5$ | CH$_3$ |
| 4 | F | Cl | H | H | CO$_2$H | CH$_3$ |
| 5 | F | Cl | H | H | CO$_2$CH$_3$ | CH$_3$ |
| 6 | F | Cl | H | H | CO$_2$C$_2$H$_5$ | CH$_3$ |
| 7 | F | Cl | H | H | CO$_2$C$_3$H$_7$ | CH$_3$ |
| 8 | F | Cl | H | H | CO$_2$C$_4$H$_9$ | CH$_3$ |
| 9 | F | Cl | H | H | CO$_2$(cyclo-C$_3$H$_5$) | CH$_3$ |
| 10 | F | Cl | H | H | CO$_2$(iso-C$_3$H$_7$) | CH$_3$ |

TABLE 1-continued

| No. | R₃ | R₄ | R₇ | R₈ | R₉ | R₁₀ |
|---|---|---|---|---|---|---|
| 11 | F | Cl | H | H | CO₂(tert-C₄H₉) | CH₃ |
| 12 | F | Cl | H | H | CO₂CH₂C≡CH | CH₃ |
| 13 | F | Cl | H | H | CO₂CH₂CH=CH₂ | CH₃ |
| 14 | F | Cl | H | H | CO₂CH₂C(CH₃)=CH₂ | CH₃ |
| 15 | F | Cl | H | H | CO₂CH₂CH₂OC₂H₅ | CH₃ |
| 16 | F | Cl | H | H | CO₂CH₂CH₂OCH₃ | CH₃ |
| 17 | F | Cl | H | H | CO₂CH₂CH₂OCOCH₃ | CH₃ |
| 18 | F | Cl | H | H | CO₂CH₂Ph | CH₃ |
| 19 | F | Cl | H | H | CO₂CH₂(4-Cl—Ph) | CH₃ |
| 20 | F | Cl | H | H | CO₂CH₂(2,6-2F—Ph) | CH₃ |
| 21 | F | Cl | H | H | CO₂CH₂(2,6-2Cl—Ph) | CH₃ |
| 22 | F | Cl | H | H | CONH₂ | CH₃ |
| 23 | F | Cl | H | H | CONHCH₃ | CH₃ |
| 24 | F | Cl | H | H | CONHC₂H₅ | CH₃ |
| 25 | F | Cl | H | H | CONHC₃H₇ | CH₃ |
| 26 | F | Cl | H | H | CONH(iso-C₃H₇) | CH₃ |
| 27 | F | Cl | H | H | CONH(cyclo-C₃H₅) | CH₃ |
| 28 | F | Cl | H | H | CONH(tert-C₄H₉) | CH₃ |
| 29 | F | Cl | H | H | CON(CH₃)₂ | CH₃ |
| 30 | F | Cl | H | H | CON(C₂H₅)₂ | CH₃ |
| 31 | F | Cl | H | H | CON(C₃H₇)₂ | CH₃ |
| 32 | F | Cl | H | H | CONHCH₂Ph | CH₃ |
| 33 | F | Cl | H | H | 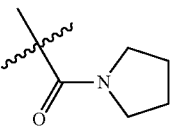 | CH₃ |
| 34 | F | Cl | H | H | 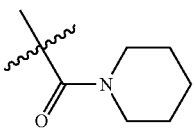 [SMILES: *C(=O)N1CCCCC1] | CH₃ |
| 35 | F | Cl | H | H | 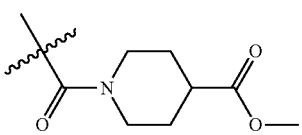 [SMILES: *C(=O)N1CCC(C(=O)OC)CC1] | CH₃ |
| 36 | F | Cl | H | H | 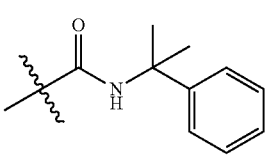 [SMILES: *C(=O)NC(C)(C)c1ccccc1] | CH₃ |
| 37 | F | Cl | H | H | 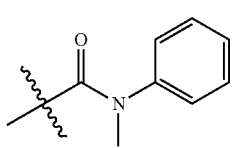 [SMILES: *C(=O)N(C)c1ccccc1] | CH₃ |
| 38 | F | Cl | H | H | 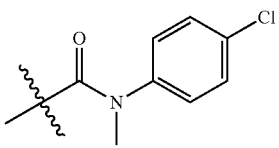 [SMILES: *C(=O)N(C)c1ccc(Cl)cc1] | CH₃ |
| 39 | F | Cl | H | H | 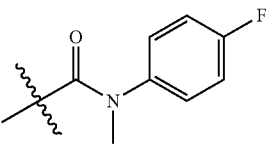 [SMILES: *C(=O)N(C)c1ccc(F)cc1] | CH₃ |

TABLE 1-continued

| No. | R₃ | R₄ | R₇ | R₈ | R₉ | R₁₀ |
|---|---|---|---|---|---|---|
| 40 | F | Cl | H | H | ![structure: acyl group with N-isopropyl-N-(4-fluorophenyl)amide] | CH₃ |
| 41 | F | Cl | H | H | CN | CH₃ |
| 42 | F | Cl | H | H | CH₂OH | CH₃ |
| 43 | F | Cl | H | H | CH₂OCOCH₃ | CH₃ |
| 44 | F | Cl | H | H | CH₂OCOC₂H₅ | CH₃ |
| 45 | F | Cl | H | H | CH₂OCO(cyco-C₃H₅) | CH₃ |
| 46 | F | Cl | H | H | CH₂OCO(iso-C₃H₇) | CH₃ |
| 47 | F | Cl | H | H | CH₂OCOC₃H₇ | CH₃ |
| 48 | F | Cl | H | H | CH₂OCOC₄H₉ | CH₃ |
| 49 | F | Cl | H | H | CH₂OCO(tert-C₄H₉) | CH₃ |
| 50 | F | Cl | H | H | CH₂OCOCH₂Cl | CH₃ |
| 51 | F | Cl | H | H | CH₂OCOCH₂CH₂Cl | CH₃ |
| 52 | F | Cl | H | H | CH₂OCO(CHCl)CH₃ | CH₃ |
| 53 | F | Cl | H | H | CH₂OCOC(CH₃)₂CH₂Cl | CH₃ |
| 54 | F | Cl | H | H | CH₂OCOCH₂CH₂SCH₃ | CH₃ |
| 55 | F | Cl | H | H | CH₂OCOCH₂CH₂Ph | CH₃ |
| 56 | F | Cl | H | H | CH₂OCO(CH═CH)Ph | CH₃ |
| 57 | F | Cl | H | H | CH₂OCOCH₂CH₂(4-Cl—Ph) | CH₃ |
| 58 | F | Cl | H | H | CH₂OCO(CH═CH)(4-Cl—Ph) | CH₃ |
| 59 | F | Cl | H | H | CH₂OCOCH₂CH₂(4-F—Ph) | CH₃ |
| 60 | F | Cl | H | H | CH₂OCO(CH═CH)(4-F—Ph) | CH₃ |
| 61 | F | Cl | H | H | CH₂OCOPh | CH₃ |
| 62 | F | Cl | H | H | CH₂OCO(4-Cl—Ph) | CH₃ |
| 63 | F | Cl | H | H | CH₂OCO(2,6-2Cl—Ph) | CH₃ |
| 64 | F | Cl | H | H | CH₂OCO(2,6-2F—Ph) | CH₃ |
| 65 | F | Cl | H | H | CH₂OCO(2,4-2Cl—Ph) | CH₃ |
| 66 | F | Cl | H | H | CH₂OCO(2-OCH₃-3,6-2Cl—Ph) | CH₃ |
| 67 | F | Cl | H | H | CH₂OCO{2-NO₂-5-[O-(2-Cl-4-CF₃—Ph)]Ph} | CH₃ |
| 68 | F | Cl | H | H | CH₂OCO{2-Cl-4-[O-(2-Cl-4-CF₃—Ph)]Ph} | CH₃ |
| 69 | F | Cl | H | H | CH₂OCO(2-Cl-4-SO₂CH₃—Ph) | CH₃ |
| 70 | F | Cl | H | H | CH₂OCO(2-SO₂CH₃-4-CF₃—Ph) | CH₃ |
| 71 | F | Cl | H | H | CH₂OCO(2-NO₂-4-SO₂CH₃—Ph) | CH₃ |
| 72 | F | Cl | H | H | CH₂OCO(2-SO₂CH₃-4-Cl—Ph) | CH₃ |
| 73 | F | Cl | H | H | CH₂OCO(2-thienyl) | CH₃ |
| 74 | F | Cl | H | H | CH₂OCO(3-CH₃-2-thienyl) | CH₃ |
| 75 | F | Cl | H | H | CH₂OCO(3-Cl-2-thienyl) | CH₃ |
| 76 | F | Cl | H | H | CH₂OCO(3-CF₃-4-pyrazolyl) | CH₃ |
| 77 | F | Cl | H | H | CH₂OCO(3-CH₃-4-pyrazolyl) | CH₃ |
| 78 | F | Cl | H | H | CH₂OCO(3-CHF₂-4-pyrazolyl) | CH₃ |
| 79 | F | Cl | H | H | CH₂OCO(3-CF₃-5-Cl-4-pyrazolyl) | CH₃ |
| 80 | F | Cl | H | H | CH₂OCO(3-CHF₂-5-Cl-4-pyrazolyl) | CH₃ |
| 81 | F | Cl | H | H | CH₂OCO(7-Cl-3-CH₃-8-quinolinyl) | CH₃ |
| 82 | F | Cl | H | H | CH₂OCO(3,7-2Cl-8-quinolinyl) | CH₃ |
| 83 | F | Cl | H | H | CH₂OCOCH₂O(2,4-2Cl—Ph) | CH₃ |
| 84 | F | Cl | H | H | CH₂OCOCH₂O(2-CH₃-4-Cl—Ph) | CH₃ |
| 85 | F | Cl | H | H | CH₂OCONHCH₃ | CH₃ |
| 86 | F | Cl | H | H | CH₂OCON(CH₃)₂ | CH₃ |
| 87 | F | Cl | H | H | CH₂OCSN(CH₃)₂ | CH₃ |
| 88 | F | Cl | H | H | CH₂OSO₂CH₃ | CH₃ |
| 89 | F | Cl | H | H | CH₂OSO₂C₂H₅ | CH₃ |
| 90 | F | Cl | H | H | CH₂OSO₂C₃H₇ | CH₃ |
| 91 | F | Cl | H | H | CH₂OSO₂CF₃ | CH₃ |
| 92 | F | Cl | H | H | CH₂OSO₂CH₂Cl | CH₃ |
| 93 | F | Cl | H | H | CH₂OSO₂Ph | CH₃ |
| 94 | F | Cl | H | H | CH₂OSO₂(4-Cl—Ph) | CH₃ |
| 95 | F | Cl | H | H | CH₂OSO₂(4-CH₃—Ph) | CH₃ |
| 96 | F | Cl | H | H | CH₂OSO₂N(CH₃)₂ | CH₃ |
| 97 | F | Cl | H | H | ![structure: CH₂-O-S(=O)₂-N(isopropyl)(methyl)] | CH₃ |
| 98 | F | Cl | H | H | CH₂Cl | CH₃ |
| 99 | F | Cl | H | H | CH₂Br | CH₃ |
| 100 | F | Cl | H | H | CH₂OPh | CH₃ |
| 101 | F | Cl | H | H | CH₂O(4-Cl—Ph) | CH₃ |
| 102 | F | Cl | H | H | CH₂O(4-F—Ph) | CH₃ |

TABLE 1-continued

| No. | $R_3$ | $R_4$ | $R_7$ | $R_8$ | $R_9$ | $R_{10}$ |
|---|---|---|---|---|---|---|
| 103 | F | Cl | H | H | $CH_2O(4\text{-}CH_3\text{—Ph})$ | $CH_3$ |
| 104 | F | Cl | H | H | $CH_2O(2\text{-}CH_3\text{-}4\text{-}Cl\text{—Ph})$ | $CH_3$ |
| 105 | F | Cl | H | H | $CH_2O(4\text{-}CF_3\text{—Ph})$ | $CH_3$ |
| 106 | F | Cl | H | H | $CH_2O(4\text{-}CF_3\text{-}2\text{-}Cl\text{—Ph})$ | $CH_3$ |
| 107 | F | Cl | H | H | $CH_2O(3\text{-}CF_3\text{—Ph})$ | $CH_3$ |
| 108 | F | Cl | H | H | $CH_2O(2,6\text{-}2Cl\text{—Ph})$ | $CH_3$ |
| 109 | F | Cl | H | H | $CH_2O(2,6\text{-}2F\text{—Ph})$ | $CH_3$ |
| 110 | F | Cl | H | H | $CH_2OCH_2Ph$ | $CH_3$ |
| 111 | F | Cl | H | H | $CH_2OCH_2(4\text{-}Cl\text{—Ph})$ | $CH_3$ |
| 112 | F | Cl | H | H | $CH_2OCH_2(4\text{-}F\text{—Ph})$ | $CH_3$ |
| 113 | F | Cl | H | H | $CH_2OCH_2(4\text{-}CH_3\text{—Ph})$ | $CH_3$ |
| 114 | F | Cl | H | H | $CH_2OCH_2(2\text{-}Cl\text{—Ph})$ | $CH_3$ |
| 115 | F | Cl | H | H | $CH_2OCH_2(4\text{-}CF_3\text{—Ph})$ | $CH_3$ |
| 116 | F | Cl | H | H | $CH_2OCH_2(3\text{-}Cl\text{—Ph})$ | $CH_3$ |
| 117 | F | Cl | H | H | $CH_2OCH_2(3\text{-}CF_3\text{—Ph})$ | $CH_3$ |
| 118 | F | Cl | H | H | $CH_2OCH_2(2,6\text{-}2Cl\text{—Ph})$ | $CH_3$ |
| 119 | F | Cl | H | H | $CH_2OCH_2(2,6\text{-}2F\text{—Ph})$ | $CH_3$ |
| 120 | F | Cl | H | H | $CO_2CH_3$ | H |
| 121 | F | Cl | H | H | $CO_2C_2H_5$ | H |
| 122 | F | Cl | H | H | $CO_2C_3H_7$ | H |
| 123 | F | Cl | H | H | $CO_2C_4H_9$ | H |
| 124 | F | Cl | H | H | $CO_2(\text{cyclo-}C_3H_5)$ | H |
| 125 | F | Cl | H | H | $CO_2(\text{iso-}C_3H_7)$ | H |
| 126 | F | Cl | H | H | $CO_2(\text{tert-}C_4H_9)$ | H |
| 127 | F | Cl | H | H | $CO_2CH_2CH_2OC_2H_5$ | H |
| 128 | F | Cl | H | H | $CO_2CH_2CH_2OCH_3$ | H |
| 129 | F | Cl | H | H | $CO_2CH_2CH_2OCOCH_3$ | H |
| 130 | F | Cl | H | H | $CO_2CH_2Ph$ | H |
| 131 | F | Cl | H | H | $CO_2CH_2(4\text{-}Cl\text{—Ph})$ | H |
| 132 | F | Cl | H | H | $CO_2CH_2(2,6\text{-}2F\text{—Ph})$ | H |
| 133 | F | Cl | H | H | $CO_2CH_2(2,6\text{-}2Cl\text{—Ph})$ | H |
| 134 | F | Cl | H | H | $CONH_2$ | H |
| 135 | F | Cl | H | H | $CONHCH_3$ | H |
| 136 | F | Cl | H | H | $CONHC_2H_5$ | H |
| 137 | F | Cl | H | H | $CONHC_3H_7$ | H |
| 138 | F | Cl | H | H | $CONH(\text{iso-}C_3H_7)$ | H |
| 139 | F | Cl | H | H | $CONH(\text{cyclo-}C_3H_5)$ | H |
| 140 | F | Cl | H | H | $CONH(\text{tert-}C_4H_9)$ | H |
| 141 | F | Cl | H | H | $CON(CH_3)_2$ | H |
| 142 | F | Cl | H | H | $CON(C_2H_5)_2$ | H |
| 143 | F | Cl | H | H | $CON(C_3H_7)_2$ | H |
| 144 | F | Cl | H | H | $CONHCH_2Ph$ | H |
| 145 | F | Cl | H | H | 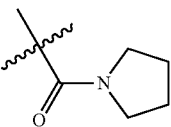 [SMILES: *C(=O)N1CCCC1] | H |
| 146 | F | Cl | H | H | 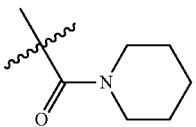 [SMILES: *C(=O)N1CCCCC1] | H |
| 147 | F | Cl | H | H | 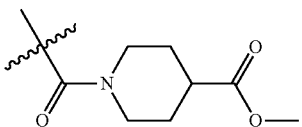 | H |
| 148 | F | Cl | H | H | 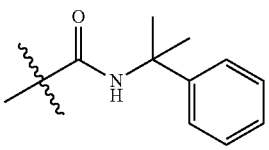 [SMILES: *C(=O)NC(C)(C)c1ccccc1] | H |
| 149 | F | Cl | H | H | 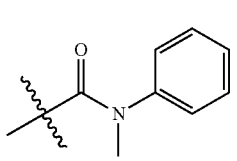 | H |

TABLE 1-continued

| No. | R₃ | R₄ | R₇ | R₈ | R₉ | R₁₀ |
|---|---|---|---|---|---|---|
| 150 | F | Cl | H | H | *N-(4-Cl-Ph)-N-CH₃-carbamoyl* (structure) | H |
| 151 | F | Cl | H | H | *N-(4-F-Ph)-N-CH₃-carbamoyl* (structure) | H |
| 152 | F | Cl | H | H | *N-(4-F-Ph)-N-isopropyl-carbamoyl* (structure) | H |
| 153 | F | Cl | H | H | CN | H |
| 154 | F | Cl | H | H | CH₂OH | H |
| 155 | F | Cl | H | H | CH₂OCOCH₃ | H |
| 156 | F | Cl | H | H | CH₂OCOC₂H₅ | H |
| 157 | F | Cl | H | H | CH₂OCO(cyclo-C₃H₅) | H |
| 158 | F | Cl | H | H | CH₂OCO(iso-C₃H₇) | H |
| 159 | F | Cl | H | H | CH₂OCOC₃H₇ | H |
| 160 | F | Cl | H | H | CH₂OCOC₄H₉ | H |
| 161 | F | Cl | H | H | CH₂OCO(tert-C₄H₉) | H |
| 162 | F | Cl | H | H | CH₂OCOCH₂Cl | H |
| 163 | F | Cl | H | H | CH₂OCOCH₂CH₂Cl | H |
| 164 | F | Cl | H | H | CH₂OCO(CHCl)CH₃ | H |
| 165 | F | Cl | H | H | CH₂OCOC(CH₃)₂CH₂Cl | H |
| 166 | F | Cl | H | H | CH₂OCOCH₂SCH₃ | H |
| 167 | F | Cl | H | H | CH₂OCOCH₂Ph | H |
| 168 | F | Cl | H | H | CH₂OCO(CH=CH)Ph | H |
| 169 | F | Cl | H | H | CH₂OCOCH₂CH₂(4-Cl—Ph) | H |
| 170 | F | Cl | H | H | CH₂OCO(CH=CH)(4-Cl—Ph) | H |
| 171 | F | Cl | H | H | CH₂OCOCH₂(4-F—Ph) | H |
| 172 | F | Cl | H | H | CH₂OCO(CH=CH)(4-F—Ph) | H |
| 173 | F | Cl | H | H | CH₂OCOPh | H |
| 174 | F | Cl | H | H | CH₂OCO(4-Cl—Ph) | H |
| 175 | F | Cl | H | H | CH₂OCO(2,6-2Cl—Ph) | H |
| 176 | F | Cl | H | H | CH₂OCO(2,6-2F—Ph) | H |
| 177 | F | Cl | H | H | CH₂OCO(2,4-2Cl—Ph) | H |
| 178 | F | Cl | H | H | CH₂OCO(2-OCH₃-3,6-2Cl—Ph) | H |
| 179 | F | Cl | H | H | CH₂OCO[2-NO₂-4-O-(2Cl-4-CF₃—Ph)] | H |
| 180 | F | Cl | H | H | CH₂OCO[2-Cl-4-O-(2Cl-4-CF₃—Ph)] | H |
| 181 | F | Cl | H | H | CH₂OCO(2-Cl-4-SO₂CH₃—Ph) | H |
| 182 | F | Cl | H | H | CH₂OCO(2-SO₂CH₃-4-CF₃—Ph) | H |
| 183 | F | Cl | H | H | CH₂OCO(2-NO₂-4-SO₂CH₃—Ph) | H |
| 184 | F | Cl | H | H | CH₂OCO(2-SO₂CH₃-4-Cl—Ph) | H |
| 185 | F | Cl | H | H | CH₂OCO(2-thienyl) | H |
| 186 | F | Cl | H | H | CH₂OCO(3-CH₃-2-thienyl) | H |
| 187 | F | Cl | H | H | CH₂OCO(3-Cl-2-thienyl) | H |
| 188 | F | Cl | H | H | CH₂OCO(3-CF₃-4-pyrazolyl) | H |
| 189 | F | Cl | H | H | CH₂OCO(3-CH₃-4-pyrazolyl) | H |
| 190 | F | Cl | H | H | CH₂OCO(3-CHF₂-4-pyrazolyl) | H |
| 191 | F | Cl | H | H | CH₂OCO(3-CF₃-5-Cl-4-pyrazolyl) | H |
| 192 | F | Cl | H | H | CH₂OCO(3-CHF₂-5-Cl-4-pyrazolyl) | H |
| 193 | F | Cl | H | H | CH₂OCO(7-Cl-3-CH₃-8-quinolinyl) | H |
| 194 | F | Cl | H | H | CH₂OCO(3,7-2Cl-8-quinolinyl) | H |
| 195 | F | Cl | H | H | CH₂OCOCH₂O(2,4-2Cl—Ph) | H |
| 196 | F | Cl | H | H | CH₂OCOCH₂O(2-CH₃-4-Cl—Ph) | H |
| 197 | F | Cl | H | H | CH₂OSO₂CH₃ | H |
| 198 | F | Cl | H | H | CH₂OSO₂C₂H₅ | H |
| 199 | F | Cl | H | H | CH₂OSO₂C₃H₇ | H |
| 200 | F | Cl | H | H | CH₂OSO₂CF₃ | H |
| 201 | F | Cl | H | H | CH₂OSO₂CH₂Cl | H |
| 202 | F | Cl | H | H | CH₂OSO₂Ph | H |
| 203 | F | Cl | H | H | CH₂OSO(4-Cl—Ph) | H |
| 204 | F | Cl | H | H | CH₂OSO₂(4-CH₃—Ph) | H |
| 205 | F | Cl | H | H | CH₂OPh | H |

TABLE 1-continued

| No. | $R_3$ | $R_4$ | $R_7$ | $R_8$ | $R_9$ | $R_{10}$ |
|---|---|---|---|---|---|---|
| 206 | F | Cl | H | H | CH$_2$O(4-Cl—Ph) | H |
| 207 | F | Cl | H | H | CH$_2$O(4-F—Ph) | H |
| 208 | F | Cl | H | H | CH$_2$O(4-CH$_3$—Ph) | H |
| 209 | F | Cl | H | H | CH$_2$O(2-CH$_3$-4-Cl—Ph) | H |
| 210 | F | Cl | H | H | CH$_2$O(4-CF$_3$—Ph) | H |
| 211 | F | Cl | H | H | CH$_2$O(4-CF$_3$-2-Cl—Ph) | H |
| 212 | F | Cl | H | H | CH$_2$O(3-CF$_3$—Ph) | H |
| 213 | F | Cl | H | H | CH$_2$O(2,6-2Cl—Ph) | H |
| 214 | F | Cl | H | H | CH$_2$O(2,6-2F—Ph) | H |
| 215 | F | Cl | H | H | CH$_2$OCH$_2$Ph | H |
| 216 | F | Cl | H | H | CH$_2$OCH$_2$(4-Cl—Ph) | H |
| 217 | F | Cl | H | H | CH$_2$OCH$_2$(4-F—Ph) | H |
| 218 | F | Cl | H | H | CH$_2$OCH$_2$(4-CH$_3$—Ph) | H |
| 219 | F | Cl | H | H | CH$_2$OCH$_2$(2-Cl—Ph) | H |
| 220 | F | Cl | H | H | CH$_2$OCH$_2$(4-CF$_3$—Ph) | H |
| 221 | F | Cl | H | H | CH$_2$OCH$_2$(3-Cl—Ph) | H |
| 222 | F | Cl | H | H | CH$_2$OCH$_2$(3-CF$_3$—Ph) | H |
| 223 | F | Cl | H | H | CH$_2$OCH$_2$(2,6-2Cl—Ph) | H |
| 224 | F | Cl | H | H | CH$_2$OCH$_2$(2,6-2F—Ph) | H |
| 225 | F | Cl | CH$_3$ | CH$_3$ | CO$_2$CH$_3$ | H |
| 226 | F | Cl | CH$_3$ | CH$_3$ | CO$_2$C$_2$H$_5$ | H |
| 227 | F | Cl | CH$_3$ | CH$_3$ | CO$_2$C$_3$H$_7$ | H |
| 228 | F | Cl | CH$_3$ | CH$_3$ | CO$_2$C$_4$H$_9$ | H |
| 229 | F | Cl | CH$_3$ | CH$_3$ | CO$_2$(cyclo-C$_3$H$_5$) | H |
| 230 | F | Cl | CH$_3$ | CH$_3$ | CO$_2$(iso-C$_3$H$_7$) | H |
| 231 | F | Cl | CH$_3$ | CH$_3$ | CO$_2$(tert-C$_4$H$_9$) | H |
| 232 | F | Cl | CH$_3$ | CH$_3$ | CO$_2$CH$_2$CH$_2$OC$_2$H$_5$ | H |
| 233 | F | Cl | CH$_3$ | CH$_3$ | CO$_2$CH$_2$CH$_2$OCH$_3$ | H |
| 234 | F | Cl | CH$_3$ | CH$_3$ | CO$_2$CH$_2$CH$_2$OCOCH$_3$ | H |
| 235 | F | Cl | CH$_3$ | CH$_3$ | CO$_2$CH$_2$Ph | H |
| 236 | F | Cl | CH$_3$ | CH$_3$ | CO$_2$CH$_2$(4-Cl—Ph) | H |
| 237 | F | Cl | CH$_3$ | CH$_3$ | CO$_2$CH$_2$(2,6-2F—Ph) | H |
| 238 | F | Cl | CH$_3$ | CH$_3$ | CO$_2$CH$_2$(2,6-2Cl—Ph) | H |
| 239 | F | Cl | CH$_3$ | CH$_3$ | CONH$_2$ | H |
| 240 | F | Cl | CH$_3$ | CH$_3$ | CONHCH$_3$ | H |
| 241 | F | Cl | CH$_3$ | CH$_3$ | CONHC$_2$H$_5$ | H |
| 242 | F | Cl | CH$_3$ | CH$_3$ | CONHC$_3$H$_7$ | H |
| 243 | F | Cl | CH$_3$ | CH$_3$ | CONH(iso-C$_3$H$_7$) | H |
| 244 | F | Cl | CH$_3$ | CH$_3$ | CONH(cyclo-C$_3$H$_5$) | H |
| 245 | F | Cl | CH$_3$ | CH$_3$ | CONH(tert-C$_4$H$_9$) | H |
| 246 | F | Cl | CH$_3$ | CH$_3$ | CON(CH$_3$)$_2$ | H |
| 247 | F | Cl | CH$_3$ | CH$_3$ | CON(C$_2$H$_5$)$_2$ | H |
| 248 | F | Cl | CH$_3$ | CH$_3$ | CON(C$_3$H$_7$)$_2$ | H |
| 249 | F | Cl | CH$_3$ | CH$_3$ | CONHCH$_2$Ph | H |
| 250 | F | Cl | CH$_3$ | CH$_3$ | 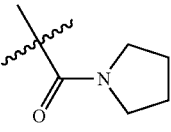 [SMILES: *C(=O)N1CCCC1] | H |
| 251 | F | Cl | CH$_3$ | CH$_3$ | 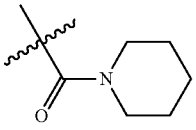 | H |
| 252 | F | Cl | CH$_3$ | CH$_3$ | 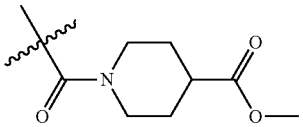 | H |
| 253 | F | Cl | CH$_3$ | CH$_3$ | 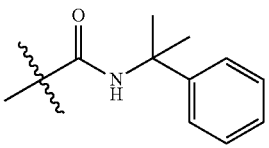 [SMILES: *C(=O)NC(C)(C)c1ccccc1] | H |

TABLE 1-continued

| No. | R₃ | R₄ | R₇ | R₈ | R₉ | R₁₀ |
|---|---|---|---|---|---|---|
| 254 | F | Cl | CH₃ | CH₃ | 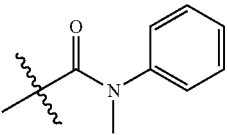 [SMILES: *C(=O)N(C)c1ccccc1] | H |
| 255 | F | Cl | CH₃ | CH₃ | 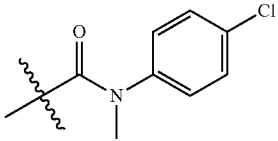 [SMILES: *C(=O)N(C)c1ccc(Cl)cc1] | H |
| 256 | F | Cl | CH₃ | CH₃ | 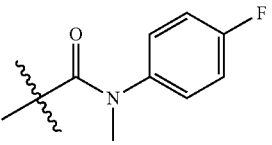 [SMILES: *C(=O)N(C)c1ccc(F)cc1] | H |
| 257 | F | Cl | CH₃ | CH₃ | 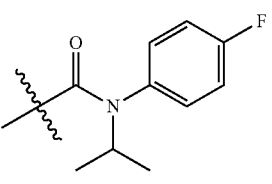 [SMILES: *C(=O)N(c1ccc(F)cc1)C(C)C] | H |
| 258 | F | Cl | H | CH₂OH | CH₃ | CH₃ |
| 259 | F | Cl | H | CH₂OCOCH₃ | CH₃ | CH₃ |
| 260 | F | Cl | H | CH₂OCOC₂H₅ | CH₃ | CH₃ |
| 261 | F | Cl | H | CH₂OCO(cyclo-C₃H₅) | CH₃ | CH₃ |
| 262 | F | Cl | H | CH₂OCO(iso-C₃H₇) | CH₃ | CH₃ |
| 263 | F | Cl | H | CH₂OCOC₃H₇ | CH₃ | CH₃ |
| 264 | F | Cl | H | CH₂OCOC₄H₉ | CH₃ | CH₃ |
| 265 | F | Cl | H | CH₂OCO(tert-C₄H₉) | CH₃ | CH₃ |
| 266 | F | Cl | H | CH₂OCOCH₂Cl | CH₃ | CH₃ |
| 267 | F | Cl | H | CH₂OCOCH₂CH₂Cl | CH₃ | CH₃ |
| 268 | F | Cl | H | CH₂OCO(CHCl)CH₃ | CH₃ | CH₃ |
| 269 | F | Cl | H | CH₂OCOC(CH₃)₂CH₂Cl | CH₃ | CH₃ |
| 270 | F | Cl | H | CH₂OCO(2-OCH₃-3,6-2Cl—Ph) | CH₃ | CH₃ |
| 271 | F | Cl | H | CH₂OCOCH₂O(2,4-2Cl—Ph) | CH₃ | CH₃ |
| 272 | F | Cl | H | CH₂OCOCH₂O(2-CH₃-4-Cl—Ph) | CH₃ | CH₃ |
| 273 | F | Cl | H | CH₂OSO₂CH₃ | CH₃ | CH₃ |
| 274 | F | Cl | H | CH₂OSO₂C₂H₅ | CH₃ | CH₃ |
| 275 | F | Cl | H | CH₂OSO₂C₃H₇ | CH₃ | CH₃ |
| 276 | F | Cl | H | CH₂OSO₂CF₃ | CH₃ | CH₃ |
| 276 | F | Cl | H | CH₂OSO₂CH₂Cl | CH₃ | CH₃ |
| 277 | F | Cl | H | CH₂OSO₂(4-Cl—Ph) | CH₃ | CH₃ |
| 278 | F | Cl | H | CH₂OSO₂(4-CH₃—Ph) | CH₃ | CH₃ |
| 279 | H | Cl | H | H | CH₃ | CH₃ |
| 280 | H | Cl | H | H | C₂H₅ | CH₃ |
| 281 | H | Cl | H | H | cyclo-C₃H₅ | CH₃ |
| 282 | H | Cl | H | H | CO₂H | CH₃ |
| 283 | H | Cl | H | H | CO₂CH₃ | CH₃ |
| 284 | H | Cl | H | H | CO₂C₂H₅ | CH₃ |
| 285 | H | Cl | H | H | CO₂C₃H₇ | CH₃ |
| 286 | H | Cl | H | H | CO₂C₄H₉ | CH₃ |
| 287 | H | Cl | H | H | CO₂(cyclo-C₃H₅) | CH₃ |
| 288 | H | Cl | H | H | CO₂(iso-C₃H₇) | CH₃ |
| 289 | H | Cl | H | H | CO₂(tert-C₄H₉) | CH₃ |
| 290 | H | Cl | H | H | CO₂CH₂C≡CH | CH₃ |
| 291 | H | Cl | H | H | CO₂CH₂CH=CH₂ | CH₃ |
| 292 | H | Cl | H | H | CO₂CH₂C(CH₃)=CH₂ | CH₃ |
| 293 | H | Cl | H | H | CO₂CH₂CH₂OC₂H₅ | CH₃ |
| 294 | H | Cl | H | H | CO₂CH₂CH₂OCH₃ | CH₃ |
| 295 | H | Cl | H | H | CO₂CH₂CH₂OCOCH₃ | CH₃ |
| 296 | H | Cl | H | H | CO₂CH₂Ph | CH₃ |
| 297 | H | Cl | H | H | CO₂CH₂(4-Cl—Ph) | CH₃ |
| 298 | H | Cl | H | H | CO₂CH₂(2,6-2F—Ph) | CH₃ |
| 299 | H | Cl | H | H | CO₂CH₂(2,6-2Cl—Ph) | CH₃ |
| 300 | H | Cl | H | H | CONH₂ | CH₃ |
| 301 | H | Cl | H | H | CONHCH₃ | CH₃ |
| 302 | H | Cl | H | H | CONHC₂H₅ | CH₃ |

TABLE 1-continued

| No. | R₃ | R₄ | R₇ | R₈ | R₉ | R₁₀ |
|---|---|---|---|---|---|---|
| 303 | H | Cl | H | H | CONHC₃H₇ | CH₃ |
| 304 | H | Cl | H | H | CONH(iso-C₃H₇) | CH₃ |
| 305 | H | Cl | H | H | CONH(cyclo-C₃H₅) | CH₃ |
| 306 | H | Cl | H | H | CONH(tert-C₄H₉) | CH₃ |
| 307 | H | Cl | H | H | CON(CH₃)₂ | CH₃ |
| 308 | H | Cl | H | H | CON(C₂H₅)₂ | CH₃ |
| 309 | H | Cl | H | H | CON(C₃H₇)₂ | CH₃ |
| 310 | H | Cl | H | H | CONHCH₂Ph | CH₃ |
| 311 | H | Cl | H | H | 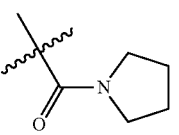 | CH₃ |
| 312 | H | Cl | H | H | 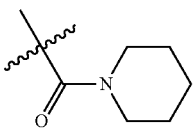 [SMILES: *C(=O)N1CCCCC1] | CH₃ |
| 313 | H | Cl | H | H | 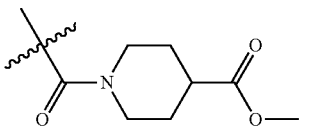 | CH₃ |
| 314 | H | Cl | H | H | 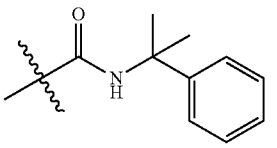 [SMILES: *C(=O)NC(C)(C)c1ccccc1] | CH₃ |
| 315 | H | Cl | H | H | 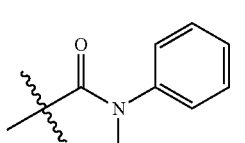 | CH₃ |
| 316 | H | Cl | H | H | 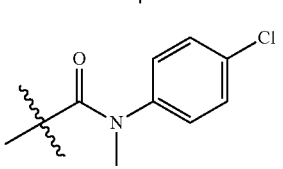 | CH₃ |
| 317 | H | Cl | H | H | 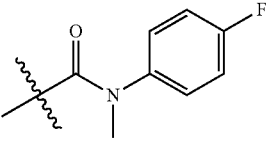 [SMILES: *C(=O)N(C)c1ccc(F)cc1] | CH₃ |
| 318 | H | Cl | H | H | 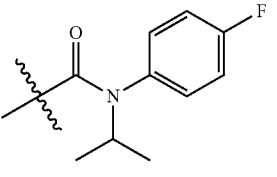 [SMILES: *C(=O)N(c1ccc(F)cc1)C(C)C] | CH₃ |
| 319 | H | Cl | H | H | CN | CH₃ |
| 320 | H | Cl | H | H | CH₂OH | CH₃ |
| 321 | H | Cl | H | H | CH₂OCOCH₃ | CH₃ |
| 322 | H | Cl | H | H | CH₂OCOC₂H₅ | CH₃ |
| 323 | H | Cl | H | H | CH₂OCO(cyclo-C₃H₅) | CH₃ |
| 324 | H | Cl | H | H | CH₂OCO(iso-C₃H₇) | CH₃ |
| 325 | H | Cl | H | H | CH₂OCOC₃H₇ | CH₃ |
| 326 | H | Cl | H | H | CH₂OCOC₄H₉ | CH₃ |

TABLE 1-continued

| No. | $R_3$ | $R_4$ | $R_7$ | $R_8$ | $R_9$ | $R_{10}$ |
|---|---|---|---|---|---|---|
| 327 | H | Cl | H | H | CH$_2$OCO(tert-C$_4$H$_9$) | CH$_3$ |
| 328 | H | Cl | H | H | CH$_2$OCOCH$_2$Cl | CH$_3$ |
| 329 | H | Cl | H | H | CH$_2$OCOCH$_2$CH$_2$Cl | CH$_3$ |
| 330 | H | Cl | H | H | CH$_2$OCO(CHCl)CH$_3$ | CH$_3$ |
| 331 | H | Cl | H | H | CH$_2$OCOC(CH$_3$)$_2$CH$_2$Cl | CH$_3$ |
| 332 | H | Cl | H | H | CH$_2$OCOCH$_2$CH$_2$SCH$_3$ | CH$_3$ |
| 333 | H | Cl | H | H | CH$_2$OCOCH$_2$CH$_2$Ph | CH$_3$ |
| 334 | H | Cl | H | H | CH$_2$OCO(CH=CH)Ph | CH$_3$ |
| 335 | H | Cl | H | H | CH$_2$OCOCH$_2$CH$_2$(4-Cl—Ph) | CH$_3$ |
| 336 | H | Cl | H | H | CH$_2$OCO(CH=CH)(4-Cl—Ph) | CH$_3$ |
| 337 | H | Cl | H | H | CH$_2$OCOCH$_2$CH$_2$(4-F—Ph) | CH$_3$ |
| 338 | H | Cl | H | H | CH$_2$OCO(CH=CH)(4-F—Ph) | CH$_3$ |
| 339 | H | Cl | H | H | CH$_2$OCOPh | CH$_3$ |
| 340 | H | Cl | H | H | CH$_2$OCO(4-Cl—Ph) | CH$_3$ |
| 341 | H | Cl | H | H | CH$_2$OCO(2,6-2Cl—Ph) | CH$_3$ |
| 342 | H | Cl | H | H | CH$_2$OCO(2,6-2F—Ph) | CH$_3$ |
| 343 | H | Cl | H | H | CH$_2$OCO(2,4-2Cl—Ph) | CH$_3$ |
| 344 | H | Cl | H | H | CH$_2$OCO(2-OCH$_3$-3,6-2Cl—Ph) | CH$_3$ |
| 345 | H | Cl | H | H | CH$_2$OCO{2-NO$_2$-5-[O-(2-Cl-4-CF$_3$—Ph)]Ph} | CH$_3$ |
| 346 | H | Cl | H | H | CH$_2$OCO{2-Cl-4-[O-(2-Cl-4-CF$_3$—Ph)]Ph} | CH$_3$ |
| 347 | H | Cl | H | H | CH$_2$OCO(2-Cl-4-SO$_2$CH$_3$—Ph) | CH$_3$ |
| 348 | H | Cl | H | H | CH$_2$OCO(2-SO$_2$CH$_3$-4-CF$_3$—Ph) | CH$_3$ |
| 349 | H | Cl | H | H | CH$_2$OCO(2-NO$_2$-4-SO$_2$CH$_3$—Ph) | CH$_3$ |
| 350 | H | Cl | H | H | CH$_2$OCO(2-SO$_2$CH$_3$-4-Cl—Ph) | CH$_3$ |
| 351 | H | Cl | H | H | CH$_2$OCO(2-thienyl) | CH$_3$ |
| 352 | H | Cl | H | H | CH$_2$OCO(3-CH$_3$-2-thienyl) | CH$_3$ |
| 353 | H | Cl | H | H | CH$_2$OCO(3-Cl-2-thienyl) | CH$_3$ |
| 354 | H | Cl | H | H | CH$_2$OCO(3-CF$_3$-4-pyrazolyl) | CH$_3$ |
| 355 | H | Cl | H | H | CH$_2$OCO(3-CH$_3$-4-pyrazolyl) | CH$_3$ |
| 356 | H | Cl | H | H | CH$_2$OCO(3-CHF$_2$-4-pyrazolyl) | CH$_3$ |
| 357 | H | Cl | H | H | CH$_2$OCO(3-CF$_3$-5-Cl-4-pyrazolyl) | CH$_3$ |
| 358 | H | Cl | H | H | CH$_2$OCO(3-CHF$_2$-5-Cl-4-pyrazolyl) | CH$_3$ |
| 359 | H | Cl | H | H | CH$_2$OCO(7-Cl-3-CH$_3$-8-quinolinyl) | CH$_3$ |
| 360 | H | Cl | H | H | CH$_2$OCO(3,7-2Cl-8-quinolinyl) | CH$_3$ |
| 361 | H | Cl | H | H | CH$_2$OCOCH$_2$(2,4-2Cl—Ph) | CH$_3$ |
| 362 | H | Cl | H | H | CH$_2$OCOCH$_2$O(2-CH$_3$-4-Cl—Ph) | CH$_3$ |
| 363 | H | Cl | H | H | CH$_2$OCONHCH$_3$ | CH$_3$ |
| 364 | H | Cl | H | H | CH$_2$OCON(CH$_3$)$_2$ | CH$_3$ |
| 365 | H | Cl | H | H | CH$_2$OCSN(CH$_3$)$_2$ | CH$_3$ |
| 366 | H | Cl | H | H | CH$_2$OSO$_2$CH$_3$ | CH$_3$ |
| 367 | H | Cl | H | H | CH$_2$OSO$_2$C$_2$H$_5$ | CH$_3$ |
| 368 | H | Cl | H | H | CH$_2$OSO$_2$C$_3$H$_7$ | CH$_3$ |
| 369 | H | Cl | H | H | CH$_2$OSO$_2$CF$_3$ | CH$_3$ |
| 370 | H | Cl | H | H | CH$_2$OSO$_2$CH$_2$Cl | CH$_3$ |
| 371 | H | Cl | H | H | CH$_2$OSO$_2$Ph | CH$_3$ |
| 372 | H | Cl | H | H | CH$_2$OSO$_2$(4-Cl—Ph) | CH$_3$ |
| 373 | H | Cl | H | H | CH$_2$OSO$_2$(4-CH$_3$—Ph) | CH$_3$ |
| 374 | H | Cl | H | H | CH$_2$OSO$_2$N(CH$_3$)$_2$ | CH$_3$ |
| 375 | H | Cl | H | H | CH$_2$Cl | CH$_3$ |
| 376 | H | Cl | H | H | CH$_2$OPh | CH$_3$ |
| 377 | H | Cl | H | H | CH$_2$O(4-Cl—Ph) | CH$_3$ |
| 378 | H | Cl | H | H | CH$_2$O(4-F—Ph) | CH$_3$ |
| 379 | H | Cl | H | H | CH$_2$O(4-CH$_3$—Ph) | CH$_3$ |
| 380 | H | Cl | H | H | CH$_2$O(2-CH$_3$-4-Cl—Ph) | CH$_3$ |
| 381 | H | Cl | H | H | CH$_2$O(4-CF$_3$—Ph) | CH$_3$ |
| 382 | H | Cl | H | H | CH$_2$O(4-CF$_3$-2-Cl—Ph) | CH$_3$ |
| 383 | H | Cl | H | H | CH$_2$O(3-CF$_3$—Ph) | CH$_3$ |
| 384 | H | Cl | H | H | CH$_2$O(2,6-2Cl—Ph) | CH$_3$ |
| 385 | H | Cl | H | H | CH$_2$O(2,6-2F—Ph) | CH$_3$ |
| 386 | H | Cl | H | H | CH$_2$OCH$_2$Ph | CH$_3$ |
| 387 | H | Cl | H | H | CH$_2$OCH$_2$(4-Cl—Ph) | CH$_3$ |
| 388 | H | Cl | H | H | CH$_2$OCH$_2$(4-F—Ph) | CH$_3$ |
| 389 | H | Cl | H | H | CH$_2$OCH$_2$(4-CH$_3$—Ph) | CH$_3$ |
| 390 | H | Cl | H | H | CH$_2$OCH$_2$(2-Cl—Ph) | CH$_3$ |
| 391 | H | Cl | H | H | CH$_2$OCH$_2$(4-CF$_3$—Ph) | CH$_3$ |
| 392 | H | Cl | H | H | CH$_2$OCH$_2$(3-Cl—Ph) | CH$_3$ |
| 393 | H | Cl | H | H | CH$_2$OCH$_2$(3-CF$_3$—Ph) | CH$_3$ |
| 394 | H | Cl | H | H | CH$_2$OCH$_2$(2,6-2Cl—Ph) | CH$_3$ |
| 395 | H | Cl | H | H | CH$_2$OCH$_2$(2,6-2F—Ph) | CH$_3$ |
| 396 | F | Cl | H | H | CO$_2$CH$_2$CF$_3$ | CH$_3$ |
| 397 | F | Cl | H | H | CO$_2$CH$_2$CH(CH$_3$)$_2$ | CH$_3$ |

TABLE 1-continued

| No. | R$_3$ | R$_4$ | R$_7$ | R$_8$ | R$_9$ | R$_{10}$ |
|---|---|---|---|---|---|---|
| 398 | F | Cl | H | H | 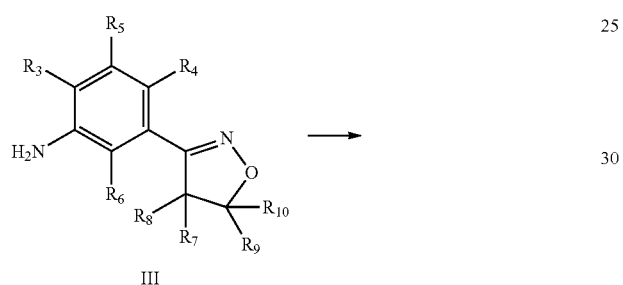 | CH$_3$ |
| 399 | H | Cl | H | H | CO$_2$CH$_2$CF$_3$ | CH$_3$ |
| 400 | H | Cl | H | H | CO$_2$CH$_2$CH(CH$_3$)$_2$ | CH$_3$ |
| 401 | H | Cl | H | H | 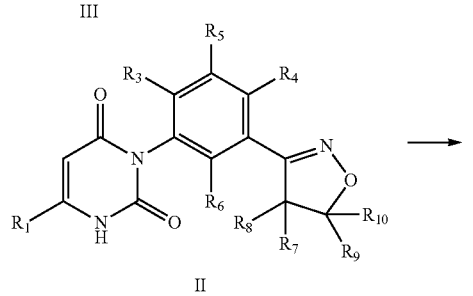 | CH$_3$ |

The compounds having general formula (I) in present invention can be prepared from amino-compounds III according to the literature method, such as U.S. Pat. Nos. 5,336,663, 6,992,044, WO2001083459, etc.

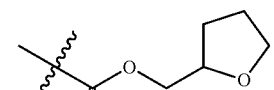

III

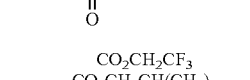

II

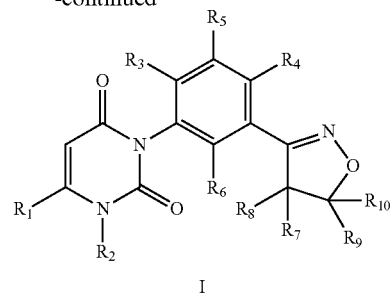

I

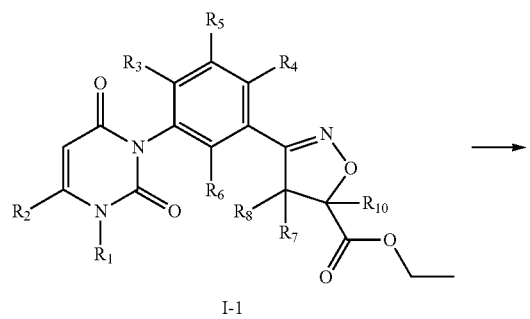

I-1

The carboxylic acids(I-2,I-2') can be prepared from the compounds I-1 or I-1' according to the literature method when R$_8$ or R$_9$ is CO$_2$C$_2$H$_5$, followed by the further reaction to form carboxylate compounds I-3 or I-3' and amides according to the literature method, the references such as US20060223848, WO2012130798, WO2014048827, WO2014048940, etc.

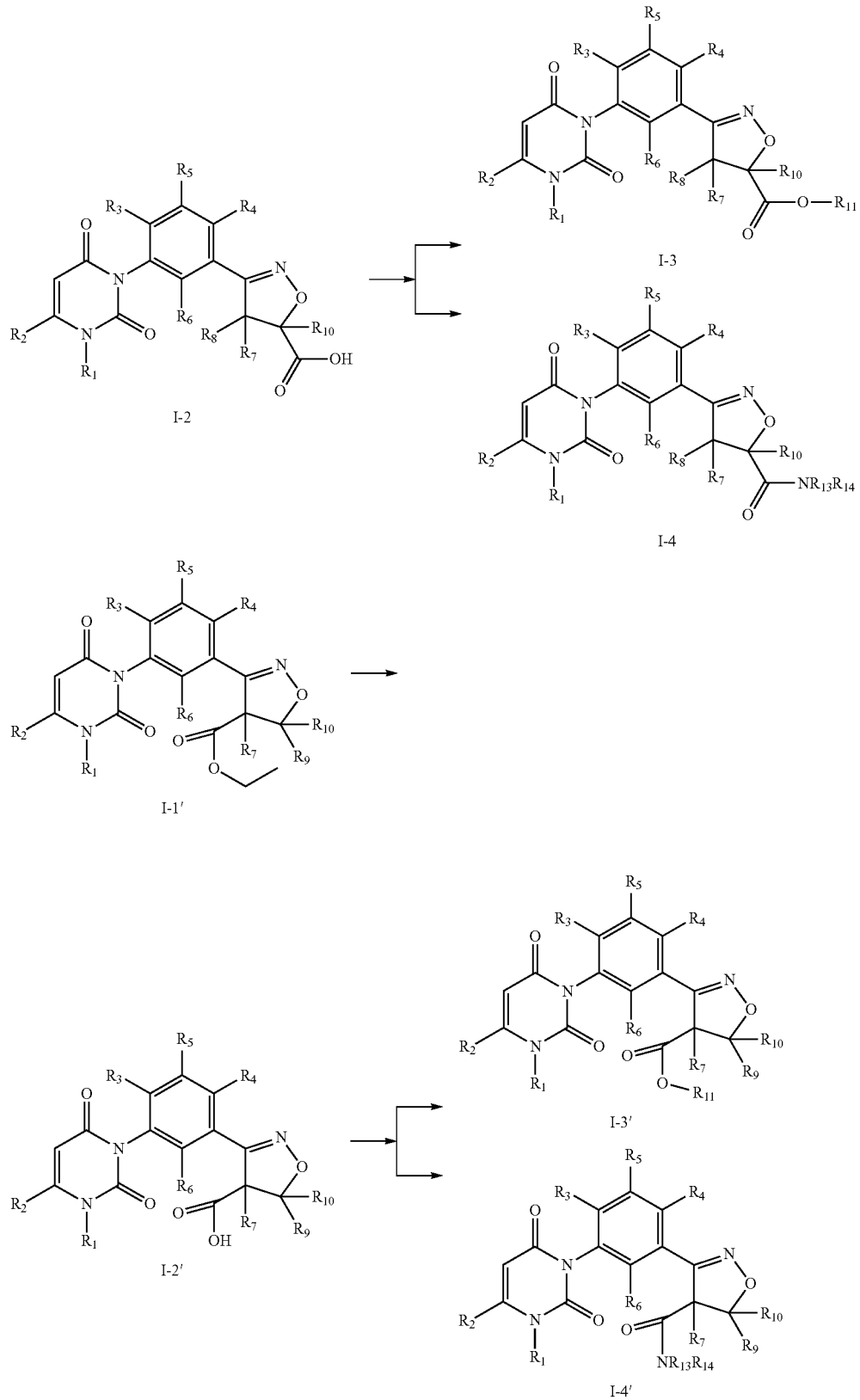

The alcohols compounds I-6 or I-6' can be prepared by reaction of the compounds I-5 or I-5' with acetyl chloride in methanol referring to synlett, 2005, 10, 1527-1530. And then the compounds I-7 or I-7' was obtained by reaction of alcohols compounds I-6 or I-6' with $R_{12}$—X which is acyl halide, benzyl halide, halogenobenzene or halogenoheteroaryl under basic conditions.

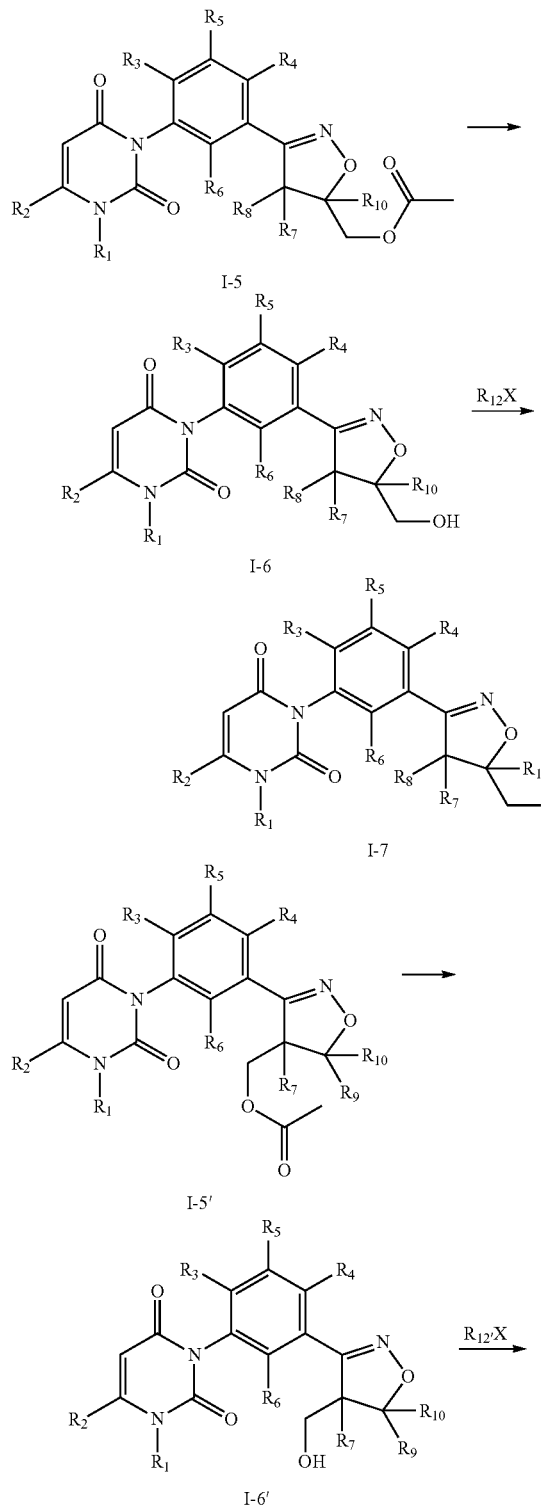

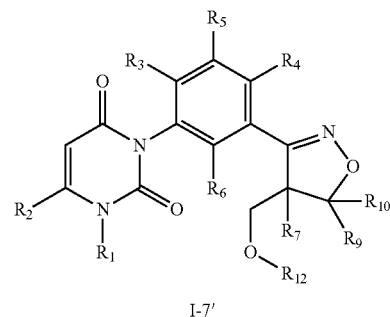

The reaction was carried out in proper solvent and the proper solvent mentioned may be selected from benzene, toluene, xylene, acetone, tetrahydrofuran, acetonitrile, N,N-dimethylformamide, N-methylpyrrolidane, dichloromethane, chloroform, dichloroethane, ethyl acetate, etc. The reaction can be carried out under base or no base conditions, and the reaction can be accelerated in the condition of base. The proper base mentioned may be selected from alkali metal hydride, such as NaH, LiH, $NaNH_2$, and so on; or alkali metal hydroxide, such as KOH, NaOH, and so on; or alkali carbonate, such as $K_2CO_3$, $Na_2CO_3$, and so on; or organo-alkali, such as pyridine, 4-dimethylaminopyridine, triethylamine, N-methylpyrrolidine, N, N-diisopropylethylamine, and so on. The proper temperature mentioned is from −10° C. to boiling point of solvent, normally the temperature is at 0 to 100° C. The reaction time is in the range of 30 minutes to 20 hours, generally being 1-10 hours.

$R_{12}$—X is commercially available. The X is leaving group selected from Cl, Br or I.

The amino-compounds III can be prepared from nitro compounds IV according to conventional methods by reductants, such as Fe, Zn, Pd/C, $SnCl_2$, and so on, referring to EP2044006, US20070155738, European Journal of Medicinal Chemistry, 2013, 65, 32-40, Synlett, 2010, (20), 3019-3022, Heterocycles, 2008, 75(1), 57-64, etc. The nitro compounds IV can be prepared from aldehydes VIII by three steps reactions according to the literature method, such as J. Agric. Food Chem. 2005, 53, 8639-8643 or WO2006090234.

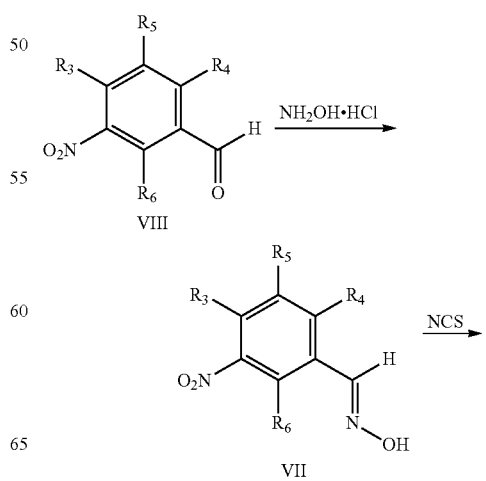

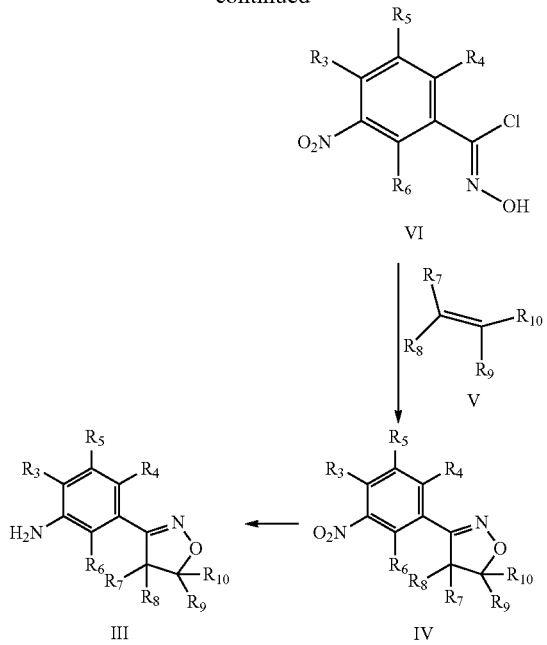

Each group of formulas is as defined above except special explanation.

The present invention compounds can effectively control weeds, such as *Echinochloa crusgalli, Setaria viridis, Cyperus difformis, Juncellus serotinus, Digitaria sangunalis, Arthraxon hispidus, Abutilon theophrasti, Zinnia elegans, Amaranthus retrofluxes, Portulaca oleracea, Xanthium sibiricum, Solanum nigrum, Cassia tora, Hibiscus trionum, Glycine soja*, an so on. They can effectively control weeds even at lower doses. The present invention compounds are also safe to wheats, corns and rices, and can used as herbicides in agriculture fields. Therefore, the present invention also includes the use of the compounds having general formula (I) as herbicides to control weeds.

A further object of the present invention relates to herbicidal compositions containing compounds having general formula (I) as active ingredient, the active component of the compositions in the weight ratio of 0.1-99%. Therefore, the present invention also includes the use of the compositions as herbicides to control weeds.

Compositions can be used in the form of dry powders, wettable powders, emulsifiable concentrates, microemulsions, pastes, granulates, solutions, suspensions, etc.: the selection of the type of composition depends on the specific use.

The compositions are prepared in the known way, for example by diluting or dissolving the active substance with a solvent medium and/or a solid diluent, optionally in the presence of surface-active agents.

Solid diluents or carriers which can be used include, for example: silica, kaolin, bentonite, talc, diatomite, dolomite, calcium carbonate, magnesia, chalk, clays, synthetic silicates, attapulgite, seppiolite and so on.

Liquid diluents which can be used include, for example, in addition to water, aromatic organic solvents (xylols or mixtures of alkylbenzols, chlorobenzene, etc.), paraffins (petroleum fractions), alcohols (methanol, propanol, butanol, octanol, glycerin), esters (ethyl acetate, isobutyl acetate, etc.), ketones (cyclohexanone, acetone, acetophenone, isophorone, ethylamylketone, etc.), amides (N,N-dimethylformamide, N-methylpyrrolidone, etc.).

Surface-active agents which can be used include salts of sodium, calcium, triethylamine or triethanolamine of alkylsulfonates, alkylarylsulfonates, polyethoxylated alkylphenols, polyethoxylated esters of sorbitol, ligninsulfonates, etc.

The compositions can also contain special additives for particular purposes, for example adhesion agents such as Arabic gum, polyvinyl alcohol, polyvinyl-pyrrolidone, etc.

The concentration of active ingredient in the above compositions can vary within a wide range depending on the active compound, the applications for which they are destined, the environmental conditions and the type of adopted formulation. In general the concentration of active ingredient ranges from 0.5 to 90%, preferably from 5 to 60%.

If required, other active ingredients being compatible with the compounds having general formula (I) can be added to the compositions, such as, other acaricides/insecticides, fungicides, plant growth regulators, antibiotics, herbicides, fertilizers.

The preparation methods of several common formulations examples in the present invention are as follows:

The preparation of suspension concentrate: in commonly used for producing the suspension concentrate, the active component in formula is 5%-35%. With water as the medium, the compound in the invention, dispersing agent, suspending agent and antifreeze are added to sanding machine for grinding to make suspension concentrate.

The preparation of water emulsion: the compound in the invention, solvent and emulsifier are mixed together, to make a homogeneous oil phase. The water is mixed with antifreeze to make a homogeneous water phase. In the high-speed stirring, the aqueous phase is added to the oil phase or oil phase is added to the aqueous phase, forming the water emulsion with good dispersity. The active component of water emulsions is generally 5%-15% in this invention. For the production of concentrated emulsions, the compounds of this invention are dissolved in one or more of the mixed solvent, and then emulsifier was added to enhance dispersion effects in the water.

The preparation of wettable powder: according to formulation requirements, the compound in the invention, surfactants and solid diluents are mixed well, after smashing through ultrafine pulverizer, that is the wettable powder products (for example, 10%-60%). For the preparation of the spraying wettable powder, the compounds of this invention can be formed the mixture with solid powder, such as clay, inorganic silicates, carbonates, as well as wetting agents, adhesives and/or dispersant agent.

The preparation of water dispersible granules: the compound in the invention and powdered solid diluents, wetting agents and adhesives are mixed to smash, kneading together with water, added to the granulation certain mesh machine for granulation, then by drying and sieving (at the scope screen). Also, the compound in the invention, dispersants, disintegrates, wetting agents and solid diluent are added to sanding machine, grinding in water to produce suspension and then spray-drying granulation, usually the content of the prepared granular products is 20%-30%.

Furthermore, the compounds having general formula (I) are also suitable for the desiccation and/or defoliation of plants.

DESCRIPTION OF THE INVENTION IN DETAIL

The following examples are illustrative of the present invention, but without being restricted thereby. (All the starting materials are commercially available except special explanation).

PREPARATION EXAMPLE

Example 1 The Preparation of Compound 6

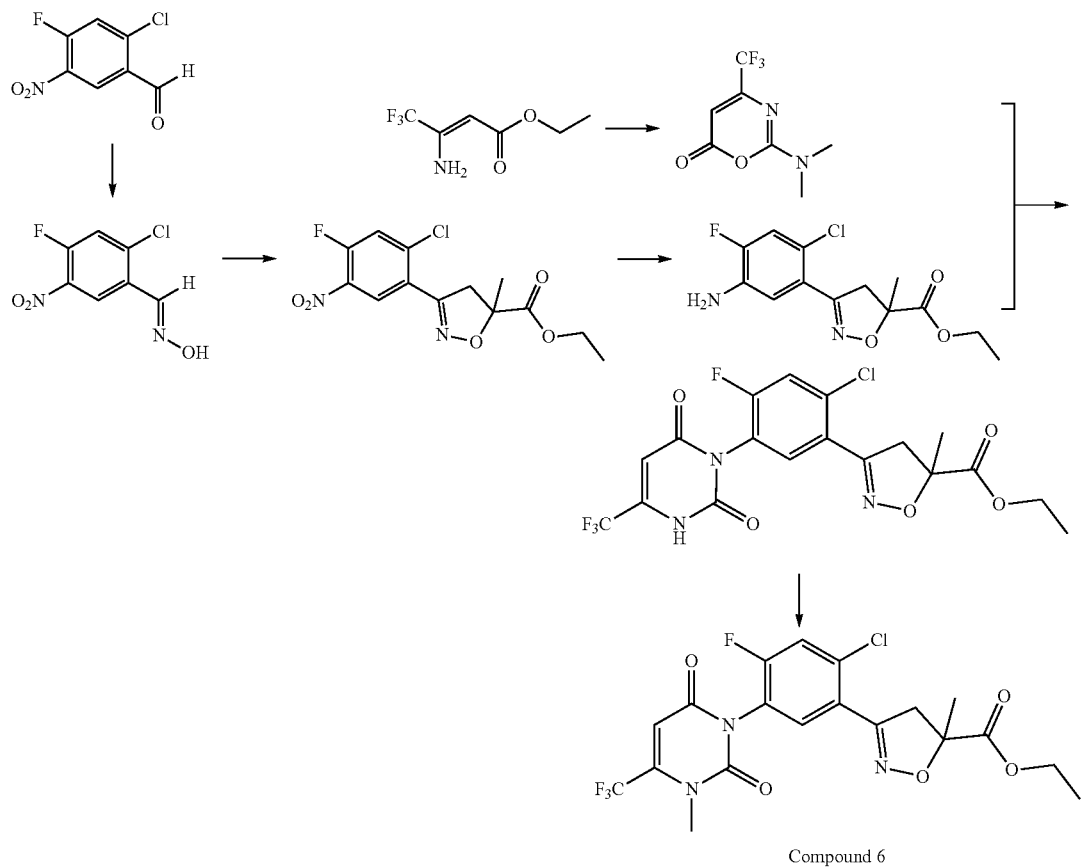

Compound 6

1) The Preparation of 2-chloro-4-fluoro-5-nitrobenzaldehyde oxime

The hydroxylamine hydrochloride aqueous solution 17.4 g (0.25 mol) was added dropwise to a solution of 2-chloro-4-fluoro-5-nitrobenzaldehyele 42 g (0.206 mol) with ethanol (200 ml) at 0° C. The mixture was stirred 2 h at room temperature, the reaction was completed by TLC monitoring. The solution was poured into water, and the precipitate solid was filtered off with suction, to give 38.3 g white solid, m.p. 103° C.

2) The Preparation of Ethyl 3-(2-chloro-4-fluoro-5-nitrophenyl)-5-methyl-4,5-dihydroisoxazole-5-carboxylate 2-chloro-4-fluoro-5-nitrobenzaldoxime 43.7 g (0.2 mol) was dissolved in 150 ml N,N-dimethylformamide, followed NCS 32 g (0.24 mol) was added in portion at 30° C. The mixture formed light yellow solution, and maintained for 1 h at 35° C., then cooled to room temperature, 300 ml dichloromethane was added, and washed twice with 1 N hydrochloric acid, then washed twice with brine. The organic layer was dried over MgSO$_4$, filtered, cooled to 0-5° C., followed the mixture of ethyl methacrylate 34.2 g(0.3 mol) and triethylamine 31 g (0.3 mol) were added dropwise to filtrate, and stirred at this temperature for 1 h. 1 N hydrochloric acid and brine were added to wash the reaction solution, the organic layer was dried over anhydrous magnesium sulfate, filtered, and concentrated in vacuo, then the residue was purified through silica column (ethyl acetate/petroleum ether (boiling point range 60-90° C.)=1:3, as an eluent) to give 57 g compound as yellow solid, m.p. 73.5° C. $^1$H-NMR spectrum(300 MHz, internal standard: TMS, solvent CDCl$_3$) δ(ppm): 1.28 (t, 3H), 1.71 (s, 3H), 3.32 (d, 1H), 3.92 (d, 1H), 4.27 (q, 2H), 7.42 (d, 1H), 8.45 (d, 1H).

3) The Preparation of 3-(5-amino-2-chloro-4-fluorophenyl)-5-methyl-4,5-dihydroisoxazole-5-carboxylate Ethyl 3-(2-chloro-4-fluoro-5-nitrophenyl)-5-methyl-4,5-dihydroisoxazole-5-carboxylate 57 g (0.18 mol) was dissolved in ethyl acetate(300 ml), then stannous chloride dihydrate 163 g (0.72 mol) was added in portion when heated. The mixture was stirred at refluxing for 8 h. After the reaction was over by TLC monitoring, the reaction mixture was poured into ice water, the mixture was adjusted to pH8 using sodium hydroxide and extracted with ethyl acetate, washed with saturated brine the extract was dried over anhydrous magnesium sulfate and concentrated under reduced pressure to give 31 g oil for next step without further purification.

4) The Preparation of 2-(dimethylamino)-4-(trifluoromethyl)-6H-1,3-oxazin-6-one

Phosgene iminium chloride 25 g(0.15 mol) was added to 100 ml trichloromethane and heated to 60° C., the mixture of ethyl 3-amino-4,4,4-trifluorocrotonate 25 g(0.14 mol) and 15 ml trichloromethane was added, the mixture was stirred at refluxing for 4 h. After the reaction was over by TLC monitoring, the mixture was cooled to room temperature and added saturated sodium bicarbonate solution. The organic layer was washed with saturated brine and dried over anhydrous magnesium sulfate and concentrated under reduced pressure, to give 30.8 g yellow solid, m.p. 81.7° C.

5) The Preparation of Ethyl 3-(2-chloro-5-(2,6-dioxo-4-(trifluoromethyl)-3,6-dihydropyrimidin-1(2H)-yl)-4-fluorophenyl)-5-methyl-4,5-dihydroisoxazole-5-carboxylate Ethyl 3-(5-amino-2-chloro-4-fluorophenyl)-5-methyl-4,5-dihydroisoxazole-5-carboxylate 13.2 g(0.046 mol) and 2-(dimethylamino)-4-(trifluoromethyl)-6H-1,3-oxazin-6-one 9.8 g(0.047 mol) were added to flask with acetic acid (100 mL) in sequence, the reaction mixture was then heated to reflux turning dark, and maintained for 6 h. The mixture was concentrated under reduced pressure, followed by adjusting to a pH of 7 using sodium bicarbonate solution, extracted with ethyl acetate, and dried over anhydrous magnesium sulfate and concentrated under reduced pressure, recrystallizated with ethanol, to give 14.5 g white solid, m.p. 105.7° C.

$^1$H-NMR spectrum(300 MHz, internal standard: TMS, solvent CDCl$_3$) δ(ppm): 1.33 (t, 3H), 1.71 (s, 3H), 3.34 (d, 1H), 3.89 (d, 1H), 4.27 (m, 2H), 6.21 (s, 1H), 7.36 (d, 1H), 7.71 (d, 1H).

6) The Preparation of Compound 6 Ethyl 3-(2-chloro-5-(2,6-dioxo-4-(trifluoromethyl)-3,6-dihydropyrimidin-1(2H)-yl)-4-fluorophenyl)-5-methyl-4,5-dihydroisoxazole-5-carboxylate 14 g (0.031 mol) and potassium carbonate 12.9 g (0.094 mol) were added to flask with N,N-dimethylformamide (150 mL) in sequence. The reaction mixture was cooled to 0° C., followed by addition of iodine methane 8.9 g (0.062 mol) dropwise, then raised temperature to room temperature, and maintained for 6 h. After the reaction was over by TLC monitoring, the mixture was poured into water and extracted with ethyl acetate, washed with saturated brine and dried over anhydrous magnesium sulfate and concentrated under reduced pressure, then the residue was purified through silica column (ethyl acetate/petroleum ether (boiling point range 60-90° C.)=⅕, as an eluent) to give 13.2 g oil.

$^1$H-NMR spectrum(300 MHz, internal standard: TMS, solvent CDCl$_3$) δ(ppm): 1.35 (t, 3H), 1.68 (s, 3H), 3.38 (d, 1H), 3.60 (s, 3H), 3.90 (d, 1H), 4.30 (m, 2H), 6.25 (s, 1H), 7.38 (d, 1H), 7.79 (d, 1H).

Example 2 The Preparation of Compound 5

Compound 5 was prepared according to the preparation process of compound 6 in example 1 to obtain oil, only replacing ethyl methacrylate with methyl methacrylate in step 2.

$^1$H-NMR spectrum(300 MHz, internal standard: TMS, solvent CDCl$_3$) δ(ppm): 1.70 (s, 3H), 3.38 (d, 1H), 3.56 (s, 3H), 3.99 (d, 1H), 4.32 (s, 3H), 6.36 (s, 1H), 7.36 (d, 1H), 7.69 (d, 1H).

Example 3 The Preparation of Compound 4

The compound 6 was added to flask with ethanol (20 mL), followed by addition of sodium hydroxide aqueous solution 2.76 g (0.069 mol). The mixture was stirred at room temperature for 4 h. After the reaction was over by TLC monitoring, the mixture was poured into water and acidified to pH 3 with 1 N HCl. The precipitate was collected by filtration, dried in vacuum to afford 9.2 g white solid, m.p. 212.3° C.

Example 4 The Preparation of Compound 10

Compound 4 0.42 g (0.89 mmol), 2-bromopropane 0.11 g(0.89 mmol), potassium carbonate 0.2 g(1.45 mmol) were added to flask with acetonitrile(20 mL) in sequence, the reaction mixture was then heated to reflux for 2 h. After the reaction was over by Thin-Layer Chromatography monitoring, the mixture was filtered and concentrated under reduced pressure, then the residue was purified through silica column (ethyl acetate/petroleum ether (boiling point range 60-90° C.)=¼, as an eluent) to give 0.2 g oil.

$^1$H-NMR spectrum(300 MHz, internal standard: TMS, solvent CDCl$_3$) δ(ppm): 1.25 (m, 6H), 1.69 (s, 3H), 3.37 (m, 1H), 3.56 (s, 3H), 3.93 (m, 1H), 5.07 (m, 1H), 6.36 (s, 1H), 7.37 (d, 1H), 7.68 (d, 1H).

Example 5 The Preparation of Compound 17

Compound 17 was prepared according to the preparation process of compound 6 in example 1 to obtain oil, only replacing ethyl methacrylate with hydroxyethyl methacrylate.

$^1$H-NMR spectrum(300 MHz, internal standard: TMS, solvent CDCl$_3$) δ(ppm): 1.72 (s, 3H), 2.61 (s, 3H), 3.38 (m, 1H), 3.56 (s, 3H), 3.95 (m, 1H), 4.05 (t, 2H), 4.30 (t, 2H), 6.37 (s, 1H), 7.34 (d, 1H), 7.69 (d, 1H).

Example 6 The Preparation of Compound 22

The compound 6 0.46 g(1 mmol) was dissolved in 15 ml tetrahydrofuran, followed by addition of ammonium hydroxide (25%) 0.42 g (3 mmol), The mixture was stirred at room temperature for 6 h. After the reaction was over by TLC monitoring, the mixture was poured into water, a precipitate was collected by filtration, dried in vacuum to afford compound 22 0.18 g as a white solid, m.p. 165.4° C.

$^1$H-NMR spectrum(300 MHz, internal standard: TMS, solvent CDCl$_3$) δ(ppm): 1.59 (s, 3H), 3.24 (s, 3H), 3.30 (d, 1H), 3.77 (d, 1H), 6.42 (s, 1H), 7.29 (s, 1H), 7.38 (d, 1H), 8.47 (d, 1H), Example 7 The Preparation of Compound 23

Compound 23 was prepared according to the preparation process of compound 22 in example 6 to obtain white solid, m.p. 225.5° C. only replacing ammonium hydroxide with ethylamine (25%).

$^1$H-NMR spectrum(300 MHz, internal standard: TMS, solvent CDCl$_3$) δ(ppm): 1.61 (s, 3H), 3.24 (d, 3H), 3.30 (d, 1H), 3.56 (s, 3H), 3.87 (d, 1H), 6.32 (s, 1H), 7.28 (s, 1H), 7.69 (d, 1H).

Example 8 The Preparation of Compound 26

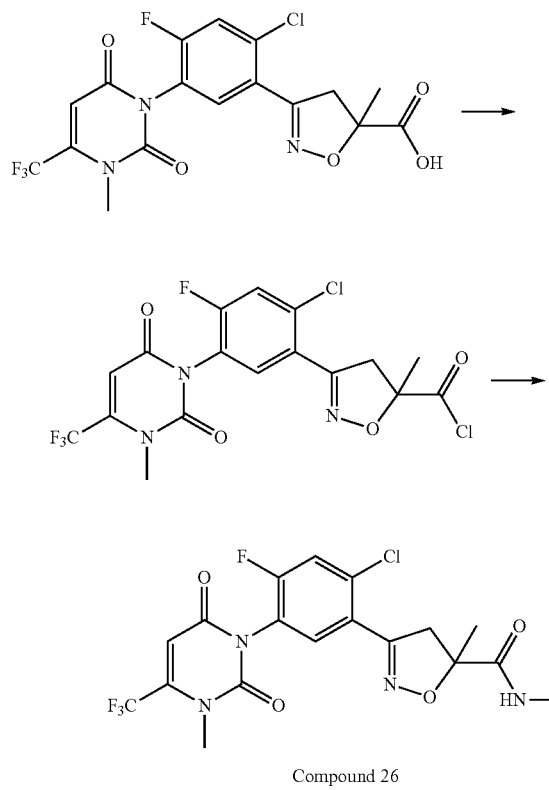

Compound 26

1) The Preparation of 3-(2-chloro-4-fluoro-5-(3-methyl-2,6-dioxo-4-(trifluoromethyl)-3,6-dihydropyrimidin-1(2H)-yl)phenyl)-5-methyl-4,5-dihydroisoxazole-5-carbonyl chloride The compound 4 9 g (0.02 mol) was dissolved in 20 ml dichloromethane, followed oxalyl chloride 7.62 g (0.06 mol) was added dropwise. The mixture was stirred at room temperature for 4 h. After the reaction was over by TLC monitoring, the mixture was concentrated under reduced pressure to give 9 g oil, for next step without further purification.

The carbonyl chloride afforded by step 1 0.45 g (0.001 mol) was dissolved in 10 ml dichloromethane, followed the mixture of isopropylamine 0.1 g (0.0015 mol) and triethylamine 0.21 g (0.002 mol) were added carefully. The mixture was stirred at room temperature for 1 h. The reaction was over by TLC monitoring, the mixture was concentrated under reduced pressure, purified through silica column (ethyl acetate/petroleum ether (boiling point range 60-90° C.)=⅛, as an eluent) to give 0.2 g yellow solid, m.p. 201.6° C.

$^1$H-NMR spectrum(300 MHz, internal standard: TMS, solvent CDCl$_3$) δ(ppm): 1.18 (m, 6H), 1.69 (s, 3H), 3.33 (d, 1H), 3.56 (s, 3H), 3.81 (d, 1H), 4.05 (m, 1H), 5.14 (m, 1H), 6.73 (s, 1H), 7.14 (d, 1H), 8.38 (d, 1H).

Example 9 The Preparation of Compound 35

Compound 35 was prepared according to the preparation process of compound 26 in example 8 to obtain yellow oil, only replacing isopropylamine with methyl isonipecotate.

$^1$H-NMR spectrum(300 MHz, internal standard: TMS, solvent CDCl$_3$) δ(ppm): 1.59 (m, 4H), 1.76 (s, 3H), 2.05 (m, 1H), 3.39 (d, 1H), 3.48 (m, 4H), 3.60 (s, 3H), 3.96 (d, 1H), 6.25 (s, 1H), 7.29 (d, 1H), 8.68 (d, 1H).

Example 10 The Preparation of Compound 42 and 43

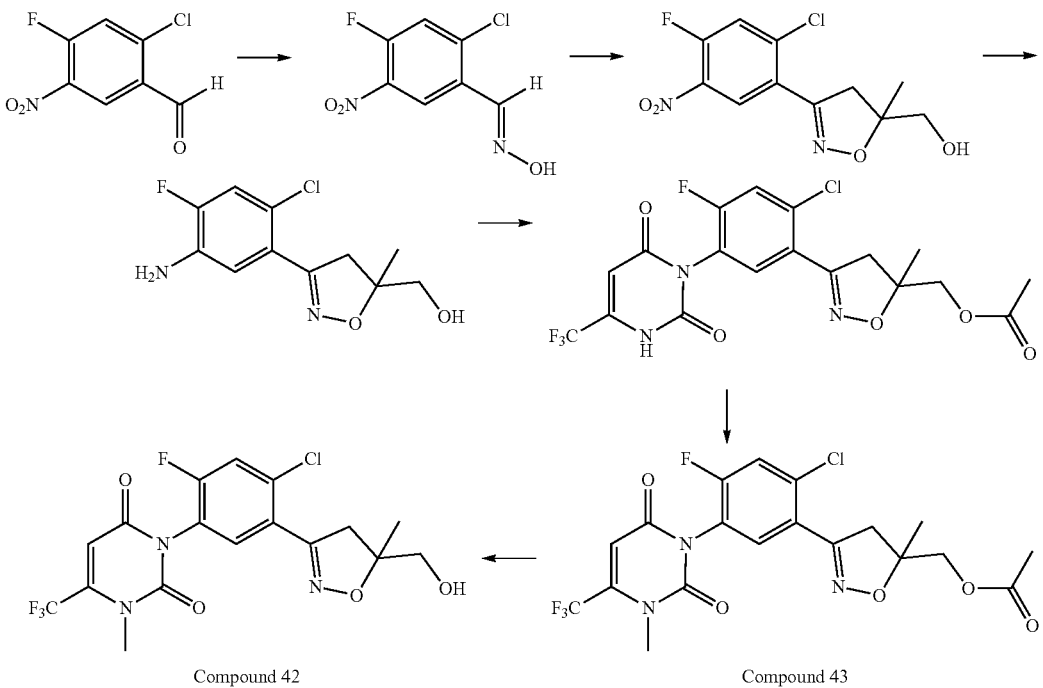

Compound 42

Compound 43

1) (E)-2-chloro-4-fluoro-5-nitrobenzaldehyde oxime was Prepared According to step 1 of Example 1

2) Preparation of (3-(2-chloro-4-fluoro-5-nitrophenyl)-5-methyl-4,5-dihydro-isoxazole-5-yl) methanol 2-chloro-4-fluoro-5-nitrobenzaldoxime 56.8 g (0.26 mol) was dissolved in 150 ml N,N-dimethylformamide, followed by addition of NCS 41.4 g (0.31 mol) in portion at 30° C. The mixture formed light yellow solution, and maintained 1 h at 35° C., then cooled to room temperature, followed by addition of 300 ml dichloromethane, and washed twice with 1 N hydrochloric acid, then washed twice with brine. The organic layer was dried over $MgSO_4$, filtered, cooled to 0-5° C., followed the mixture of methyl-2-propen-1-ol 24.5 g (0.34 mol) and triethylamine 34.4 g (0.34 mol) were added dropwise to filtrate, and stirred at this temperature for 1 h. 1 N hydrochloric acid and brine were added to wash the reaction solution, the organic layer was dried over anhydrous magnesium sulfate, filtered, and concentrated in vacuo, then the residue was purified through silica column (ethyl acetate/petroleum ether (boiling point range 60-90° C.)=1:3, as an eluent) to give 34 g compound as yellow solid, m.p. 117.1° C.

$^1$H-NMR spectrum(300 MHz, internal standard: TMS, solvent $CDCl_3$) δ(ppm): 1.47 (s, 3H), 3.18 (d, 1H), 3.62 (s, 2H), 3.79 (d, 1H), 7.43 (d, 1H), 8.42 (d, 1H).

3) Preparation of (3-(2-chloro-4-fluoro-5-aminophenyl)-5-methyl-4,5-dihydro-isoxazole-5-yl) methanol (3-(2-chloro-4-fluoro-5-nitrophenyl)-5-methyl-4,5-dihydro-isoxazole-5-yl) methanol 40 g(0.139 mol) was dissolved in 200 ml ethyl acetate, followed by addition of stannous chloride dihydrate 109.5 g (0.49 mol) in portion under heating. The mixture was stirred at reflux for 8 h. After the reaction was over by TLC monitoring, the reaction mixture was poured into ice water, the mixture was adjusted to a pH of 8 using sodium hydroxide and extracted with ethyl acetate, washed with saturated brine, the extract was dried over anhydrous magnesium sulfate and concentrated under reduced pressure to give 27 g oil for next step without further purification.

4) Preparation of (3-(2-chloro-5-(2,6-dioxo-4-trifluoromethyl-3,6-dihydropyrimidine-1-(2H)-yl)-4-flourophenyl)-5-methyl-4,5-dihydro-isoxazole-5-yl) methyl acetate (3-(2-chloro-4-fluoro-5-aminophenyl)-5-methyl-4,5-dihydro-isoxazole-5-yl) methanol 19.5 g (0.0754 mol) and 2-(dimethylamino)-4-(trifluoromethyl)-6H-1,3-oxazin-6-one 17.3 g (0.083 mol, step 4 of example 1) were added to flask with 100 mL acetic acid in sequence, the reaction mixture was then heated to reflux turning dark, and maintained for 6 h. The mixture was concentrated under reduced pressure, followed by adjusting to a pH of 7 using sodium bicarbonate solution, extracted with ethyl acetate, and dried over anhydrous magnesium sulfate and concentrated under reduced pressure to give 30.5 g white solid, m.p. 80.2° C.

$^1$H-NMR spectrum(300 MHz, internal standard: TMS, solvent $CDCl_3$) δ(ppm): 1.39 (s, 3H), 2.01 (s, 3H), 3.27 (d, 1H), 3.48 (d, 1H), 4.13 (m, 2H), 6.21 (s, 1H), 7.61 (d, 1H), 7.78 (d, 1H), 12.78 (s, 1H).

5) The Preparation of Compound 43

(3-(2-chloro-5-(2,6-dioxo-4-trifluoromethyl-3,6-dihydropyrimidine-1-(2H)-yl)-4-fluorophenyl)-5-methyl-4,5-dihydro-isoxazole-5-yl) methyl acetate 30.5 g(0.066 mol) and potassium carbonate 18.2 g (0.132 mol) were added to flask with N,N-dimethylformamide (150 mL) in sequence. The reaction mixture was cooled to 0° C., followed by addition of iodine methane 11.4 g(0.08 mol) dropwise, then raised temperature to room temperature, and maintained for 6 h. After the reaction was over by TLC monitoring, the mixture was poured into water and extracted with ethyl acetate, washed with saturated brine and dried over anhydrous magnesium sulfate and concentrated under reduced pressure, then the residue was purified through silica column (ethyl acetate/petroleum ether (boiling point range 60-90° C.)=⅕, as an eluent) to give 25 g oil.

$^1$H-MMR spectrum(300 MHz, internal standard; TMS, solvent $CDCl_3$) δ(ppm): 1.41 (s, 3H), 2.03 (s, 3H), 3.25 (d, 1H), 3.50 (d, 1H), 3.62 (s, 3H), 3.87 (m, 2H), 6.21 (s, 1H), 7.51 (d, 1H), 7.70 (d, 1H).

6) The Preparation of Compound 42

Compound 40 25 g (0.052 mol) was added to flask with 100 ml methanol, followed by addition of acetyl chloride 0.59 g (0.0078 mol) dropwise, the reaction mixture was stirred at room temperature for 8 h. After the reaction was over by TLC monitoring, the mixture was concentrated under reduced pressure, then the residue was added dichloromethane, sodium hydrogen carbonate solution, organic phase was dried over anhydrous magnesium sulfate and concentrated under reduced pressure, then the residue was purified through silica column (ethyl acetate/petroleum ether (boiling point range 60-90° C.)=¼, as an eluent) to give 15.4 g white solid, m.p. 161° C.

$^1$H-NMR spectrum(300 MHz, internal standard: TMS, solvent $CDCl_3$) δ(ppm): 1.43 (s, 3H), 3.20 (m, 1H), 3.59 (s, 3H), 3.73 (m, 1H), 3.79 (m, 2H), 6.40 (s, 1H), 7.37 (m, 1H), 7.68 (m, 1H).

Example 11 The Preparation of Compound 45

Compound 42 0.4 g (0.9 mmol) and cyclopropanecarbonyl chloride 0.1 g(0.9 mmol) were added to flask with 15 ml toluen in sequence, followed by addition of triethylamine 0.14 g(1.35 mmol), then the reaction mixture was stirred at room temperature for 2 h. After the reaction was over by TLC monitoring, the mixture was concentrated under reduced pressure, then the residue was purified through silica column (ethyl acetate/petroleum ether (boiling point range 60-90° C.)=¼, as an eluent) to give 0.5 g buff oil.

$^1$H-NMR spectrum(300 MHz, internal standard: TMS, solvent $CDCl_3$) δ(ppm): 0.87 (2H, q), 1.01 (2H, q), 1.40 (s, 3H), 1.62 (1H, m), 3.24 (1H, d), 3.48 (1H, d), 3.56 (3H, s), 4.17 (2H, t), 6.36 (1H, s), 7.35 (1H, d), 7.67 (1H, d).

Example 12 The Preparation of Compound 99

Compound 42 2 g (4.6 mmol) and carbon tetrabromide 2.3 g(6.8 mmol) were added to flask with 30 ml dichloromethane in sequence, followed by addition of triphenylphosphine 1.8 g(6.8 mmol) at room temperature, the reaction mixture was then heated to reflux after 30 min, maintained additional 6 h, the reaction was over by TLC monitoring, the mixture was cooled to room temperature, filtrated, concentrated under reduced pressure, then the residue was purified through silica column (ethyl acetate/petroleum ether (boiling point range 60-90° C.)=⅕, as an eluent) to give 0.59 g buff oil.

$^1$H-NMR spectrum(300 MHz, internal standard: TMS, solvent $CDCl_3$) δ(ppm): 1.43 (s, 3H), 3.28 (m, 1H), 3.62 (s, 3H), 3.68 (m, 1H), 3.85 (m, 2H), 6.43 (s, 1H), 7.39 (m, 1H), 7.70 (m, 1H).

Example 13 The Preparation of Compound 320 and 321

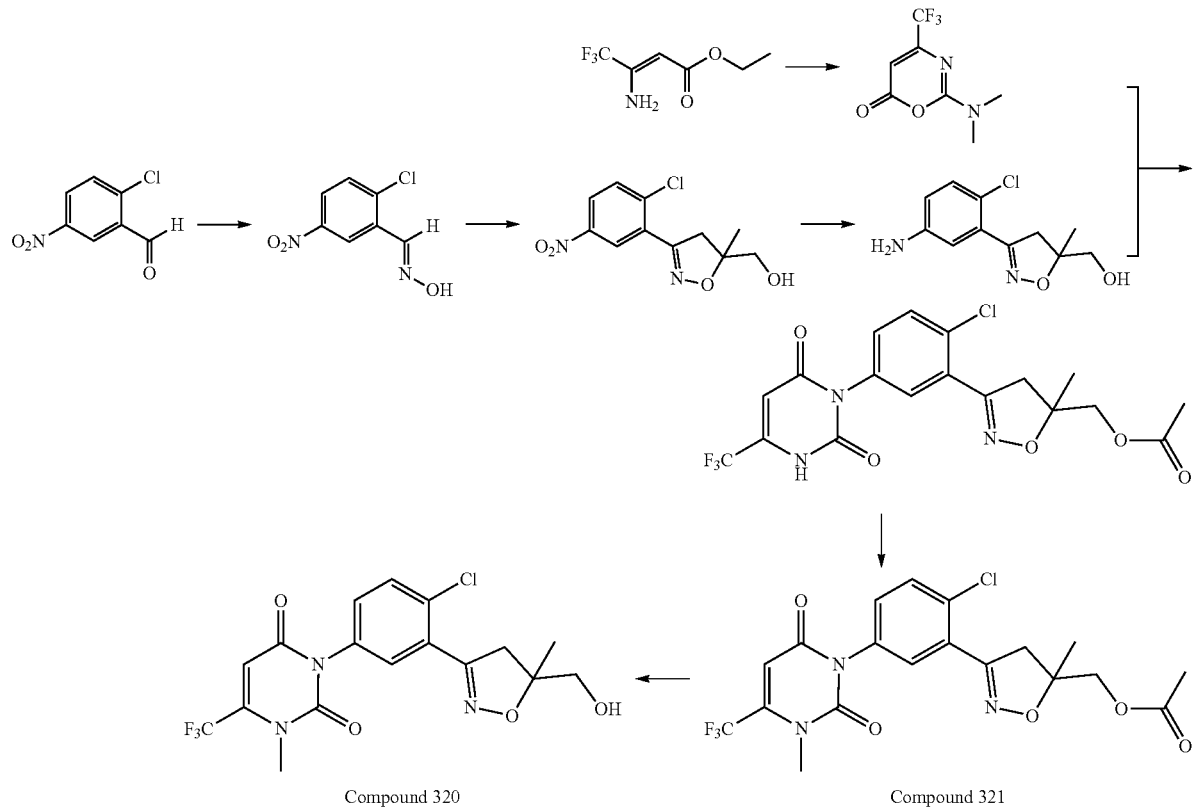

Compound 320 and 321 were prepared according to the preparation process of compound 42 and 43 in example 10, only replacing 2-chloro-4-fluoro-5-nitrobenzaldehyde with 2-chloro-5-nitrobenzaldehyde.

Compound 46, 50, 54, 55, 66, 67, 83, 88, 90, 96, 323, 324, 328, 329, 332, 333, 345 and 366 were prepared according to the preparation process of example 11.

Compound 282 was prepared according to the preparation process of compound 4 in example 3.

Compound 7, 8, 15, 16, 284, 396, 397 and 398 was prepared according to the preparation process of compound 6 in example 1.

Compound 286 and 290 was prepared according to the preparation process of compound 6 in example 4.

Physical properties and $^1$H NMR spectrum of some compounds of this invention refer to Table 2.

TABLE 2

| No. | Physical properties and $^1$H NMR spectrum (300 MHz, internal standard TMS, solvent CDCl$_3$) |
|---|---|
| 7 | Oil; δppm 0.96 (3H, t), 1.71 (3H, s), 1.73 (3H, m), 3.38 (1H, d), 3.55 (3H, s), 4.02 (1H, d), 4.17 (2H, t), 6.36 (1H, s), 7.35 (1H, d), 7.68 (1H, d) |
| 8 | Oil; δppm 0.94 (3H, t), 1.38 (4H, m), 1.71 (3H, s), 3.37 (1H, d), 3.55 (3H, s), 3.99 (1H, d), 4.21 (2H, t), 6.36 (1H, s), 7.35 (1H, d), 7.68 (1H, d) |
| 15 | Oil; δppm 1.18 (3H, t), 1.72 (3H, s), 2.91 (1H, d), 3.38 (2H, m), 3.51 (3H, s), 3.67 (2H, t), 3.99 (1H, d), 4.35 (2H, t), 6.36 (1H, s), 7.34 (1H, d), 7.67 (1H, d) |
| 16 | Oil; δppm 1.29 (3H, t), 1.71 (3H, s), 2.95 (d, 1H), 3.55 (s, 3H), 3.82 (d, 1H), 4.00 (t, 2H), 4.27 (t, 2H), 6.35 (s, 1H), 7.34 (d, 1H), 7.68 (d, 1H) |
| 46 | Oil; δppm 1.15-1.21 (6H, m), 1.51 (3H, s), 2.57-2.61 (1H, m), 3.26 (1H, d), 3.48 (1H, d), 3.66 (3H, s), 4.12-4.23 (2H, dd), 6.37 (1H, s), 7.34 (1H, d), 7.66 (1H, d) |
| 50 | Oil; δppm 1.57 (3H, s), 3.25-3.34 (2H, dd), 3.57 (3H, s), 4.11 (2H, d), 4.21-4.35 (2H, dd), 6.38 (1H, s), 7.36 (1H, d), 7.36 (1H, d) |
| 54 | Oil; δppm 1.51 (3H, s), 2.09 (3H, s), 2.60-2.83 (6H, m), 3.55 (3H, s), 4.15-4.26 (2H, dd), 6.36 (1H, s), 7.34 (1H, d), 7.65 (1H, d) |
| 55 | Oil; δppm 1.45 (3H, s), 2.68 (2H, m), 3.23 (2H, d), 3.36 (2H, d), 3.54 (3H, s), 4.12-4.18 (2H, dd), 6.34 (1H, s), 7.17-7.25 (5H, m), 7.35 (1H, d), 7.66 (1H, d) |
| 66 | Oil; δppm 1.57 (3H, s), 3.26 (1H, d), 3.56 (3H, s), 3.61 (1H, d), 3.90 (3H, s), 4.41-4.53 (2H, dd), 6.37 (1H, s), 7.12 (1H, d), 7.34 (2H, m), 7.63 (1H, m) |
| 67 | Oil; δppm 1.53 (3H, s), 3.18-3.29 (2H, dd), 3.55 (3H, s), 4.34-4.44 (2H, dd), 6.36 (1H, s), 7.06 (1H, m), 7.15 (1H, m), 7.24 (1H, d), 7.35 (1H, d), 7.62 (2H, d), 7.80 (1H, d), 8.03 (1H, d) |

TABLE 2-continued

| No. | Physical properties and $^1$H NMR spectrum (300 MHz, internal standard TMS, solvent CDCl$_3$) |
|---|---|
| 83 | Oil; δppm 1.49 (3H, s), 3.25-3.44 (2H, dd), 3.56 (3H, s), 4.20-4.37 (2H, dd), 4.73 (2H, d), 6.36 (1H, s), 6.78 (1H, d), 7.15 (1H, m), 7.36 (2H, t), 7.42 (1H, m) |
| 88 | Oil; δppm 1.55 (3H, s), 3.15 (3H, s), 3.26 (1H, m), 3.61 (3H, s), 3.67 (1H, m), 4.25-4.33 (2H, dd), 6.37 (1H, s), 7.35 (1H, d), 7.63 (1H, d) |
| 90 | Oil; δppm 1.06 (3H, t), 1.57 (3H, s), 1.92 (2H, m), 3.16 (2H, m), 3.25 (2H, m), 3.62 (3H, s), 4.23 (2H, s), 6.37 (1H, s), 7.36 (1H, d), 7.63 (1H, d) |
| 96 | oil; δppm 1.55 (3H, s), 3.06 (3H, s), 3.31 (3H, s), 3.44-3.56 (2H, dd), 3.61 (3H, s), 4.47-4.63 (2H, dd), 6.37 (1H, s), 7.34 (2H, s), 7.68 (1H, d). |
| 282 | Oil; δppm 1.56 (3H, s), 3.02 (1H, d), 3.23 (1H, d), 3.43 (3H, s), 6.36 (1H, s), 7.32 (2H, m), 7.47 (1H, d), 8.05 (1H, s) |
| 284 | Oil; δppm 1.14 (3H, t), 1.67 (3H, s), 3.22 (2H, d), 3.55 (2H, d), 3.66 (3H, s), 4.22 (2H, q), 6.36 (1H, s), 7.46 (1H, d), 7.63 (1H, d), 7.73 (1H, d) |
| 286 | Oil; δppm 0.94 (3H, t), 1.26 (2H, t), 1.43 (2H, t), 1.67 (3H, s), 3.38 (1H, d), 4.02 (1H, d), 4.15 (3H, s), 4.21 (2H, t), 6.36 (1H, s), 7.13 (1H, s), 7.56 (2H, m) |
| 290 | Oil; δppm 1.74 (3H, s), 3.46 (1H, d), 3.55 (3H, s), 4.00 (1H, d), 4.78 (2H, d), 6.36 (1H, s), 7.54 (2H, m), 8.02 (1H, s) |
| 320 | Oil; δppm 1.52 (3H, s), 3.03 (1H, d), 3.24 (1H, d), 3.46 (3H, s), 4.52 (1H, s), 6.36 (1H, s), 7.33 (2H, m), 7.48 (1H, d) |
| 321 | oil; δppm 1.48 (3H, s), 2.07 (3H, s), 2.85 (2H, d), 3.25 (2H, d), 3.51 (3H, s), 4.15 (2H, dd), 6.34 (1H, s), 7.19 (1H, dd), 7.55 (1H, dd) |
| 323 | Oil; δppm 0.88 (2H, m), 1.26 (2H, m), 1.51 (3H, s), 1.66 (1H, m), 3.27 (1H, d), 3.49 (1H, d), 3.57 (3H, s), 4.17 (2H, dd), 6.36 (1H, s), 7.22 (1H, m), 7.58 (2H, m) |
| 324 | Oil; δppm 1.13 (6H, m), 1.51 (3H, s), 2.60 (1H, m), 3.34 (2H, dd), 3.55 (3H, s), 4.18 (2H, m), 6.37 (1H, s), 7.20 (1H, m), 7.58 (2H, m) |
| 328 | Oil; δppm 1.54 (3H, s), 3.31 (1H, d), 3.53 (1H, d), 3.61 (3H, s), 4.10 (2H, d), 4.28 (2H, dd), 6.37 (1H, s), 7.22 (1H, d), 7.57 (2H, s) |
| 329 | Oil; δppm 1.53 (3H, s), 2.05 (2H, t), 2.62 (2H, d), 3.29 (1H, d), 3.53 (1H, d), 4.27 (2H, dd), 6.37 (1H, s), 7.21 (1H, d), 7.57 (2H, m) |
| 332 | Oil; δppm 1.51 (3H, s), 2.05 (3H, s), 2.12 (2H, d), 2.66 (2H, m), 3.25 (1H, d), 3.52 (1H, d), 3.55 (3H, s), 4.18 (2H, d), 6.34 (1H, s), 7.19 (1H, d), 7.54 (2H, m) |
| 333 | Oil; δppm 1.46 (3H, s), 2.67 (2H, t), 3.96 (2H, t), 3.23 (1H, d), 3.40 (1H, d), 3.52 (3H, s), 6.36 (1H, s), 7.19 (5H, m), 7.32 (2H, m), 7.56 (1H, s). |
| 345 | Oil; δppm 1.55 (3H, s), 3.22 (2H, dd), 3.56 (3H, s), 4.40 (2H, dd), 6.36 (1H, s), 7.15 (4H, m), 7.53 (2H, m), 7.59 (1H, m), 7.80 (1H, s), 8.02 (1H, d) |
| 366 | Oil; δppm 1.54 (3H, s), 2.05 (1H, d), 3.07 (1H, d), 3.15 (3H, s), 3.75 (2H, d), 4.02 (3H, s), 6.36 (1H, s), 7.21 (1H, m), 7.56 (2H, m) |
| 396 | Oil; δppm 1.70 (3H, s), 3.38 (1H, d), 3.56 (3H, s), 3.94 (1H, d), 4.29 (2H, m), 6.36 (1H, s), 7.35 (1H, d), 7.69 (1H, d) |
| 397 | Oil; δppm 0.95 (6H, d), 1.72 (3H, s), 2.01 (1H, m), 3.38 (1H, d), 3.56 (3H, s), 3.94 (1H, d), 4.07 (2H, m), 6.36 (1H, s), 7.35 (1H, d), 7.67 (1H, d) |
| 398 | Oil; δppm 1.72 (3H, s), 1.93 (4H, m), 3.37 (1H, d), 3.56 (3H, s), 3.81 (2H, m), 4.03 (1H, d), 4.16 (1H, m) 4.23 (2H, m), 6.36 (1H, s), 7.35 (1H, d), 7.67 (1H, d) |

FORMULATION EXAMPLE (BASE ON 100% ACTIVE INGREDIENT (WEIGHT/WEIGHT %))

Example 14 35% Emulsifiable Concentrate

| | |
|---|---|
| Compound 6 | 35% |
| phosphorous acid | 10% |
| ethoxylated triglyceride | 15% |
| cyclohexanone | Make up to 100% |

The phosphorous acid was dissolved in cyclohexanone, followed by addition of compound 6 and ethoxylated triglycerides to form clear solution.

Example 15 60% Wettable Powders

| | |
|---|---|
| Compound 43 | 60% |
| sodium dodecylsulphate | 2% |
| sodium lignosulphonate | 9% |
| kaolin | Make up to 100% |

Compound 43, sodium dodecylsulphate, sodium lignosulphonate and kaolin are fully mixed, after smashing through ultrafine pulverizer to the required standard.

Example 16 60% Water Dispersible Granules

| | |
|---|---|
| Compound 6 | 60% |
| Naphthalene sulfonate formaldehyde condensate | 12% |
| N-methyl-N-oil acyl-bovine sodium | 8% |
| Polyvinylpyrrolidone | 2% |
| Carboxymethyl cellulose | 2% |
| Kaolin | Make up to 100% |

Compound 6 and other components are mixed and smashed, then kneaded together with water, added to the granulation 10-100 mesh machine for granulation, finally dried and sieved (at the scope screen).

Example 17 40% Suspension Concentrate

| | |
|---|---|
| Compound 55 | 40% |
| Glycol | 10% |
| Nonylphenols polyethylene glycol ether | 6% |
| Lignin sulfonate | 10% |
| Carboxymethyl cellulose | 1% |
| 37% formaldehyde aqueous solution | 0.2% |
| 75% of silicone oil water emulsion | 0.8% |
| water | Make up to 100% |

Fully mixing compound 55 and other components, suspension concentrate can be obtained, and then any required concentration dilution can be obtained by diluting the above obtained concentrated suspension with water.

Test of Biological Activity

Example 18 Bioassay of Herbicidal Activity in Greenhouse

Determination of herbicidal activity of compounds of the present invention against weeds was carried out by the following procedures:

Seeds of monocotyledonous and dicotyledonous weeds were sown in nutrition soil in paper pot (7 cm diameter), covered with soil in 1 cm and grown in the greenhouse under good growth conditions (temperature, atmospheric humidity, water supply). The compounds of the present invention as emulsifiable concentrate, were applied in pre-emergence and post-emergence treatment by track sprayer (Engineer Research Ltd., pressure 1.95 kg/cm$^2$, volume 500 L/hm$^2$, track speed 1.48 km/h). Pre-emergence treatment was conducted after seeding 24 hours and post-emergence treatment was done when the respective weeds reached predetermined leaf stage (grass weed 2- to 3-leaf stage, broad-leaf weed 2- to 4-leaf stage), the state of growth of the respective weeds were visually observed to determine the growth inhibition rate (%) in accordance with the following evaluation standard.

Growth inhibition rate (%): 0=no discernible action: 100=all weeds dead or not emerged.

The results of general screening showed that compounds 4, 5, 6, 7, 8, 10, 15, 16, 17, 22, 23, 26, 35, 42, 43, 45, 46, 50, 54, 55, 66, 67, 83, 88, 90, 96, 99, 282, 284, 286, 290, 320, 321, 323, 324, 328, 329, 332, 333, 345, 366, 396, 397, 398 had a good pre-emergence and post-emergence herbicidal activity against broad-leaf weeds and grass weeds at 1000 g a.i./hm$^2$.

Further screening results in Table 3.

TABLE 3

| | | Herbcicidal Evaluation | | | | | | | |
|---|---|---|---|---|---|---|---|---|---|
| | | Pre-emergence treatment | | | | Post-emergence treatment | | | |
| Compound | Dose g a.i./hm$^2$ | Zinnia elegans Jacq. | Abutilon theophrasti Medic. | Setaria glauca (L.) Beauv. | Echinochloa crus-galli (L.) Beauv. | Zinnia elegans Jacq. | Abutilon theophrasti Medic. | Setaria glauca (L.) Beauv. | Echinochloa crus-galli (L.) Beauv. |
| 4 | 37.5 | 0 | 10 | 0 | 0 | 95 | 50 | 20 | 15 |
|   | 150 | 5 | 15 | 5 | 0 | 100 | 98 | 70 | 25 |
|   | 600 | 20 | 40 | 30 | 10 | 100 | 98 | 100 | 85 |
| 5 | 7.5 | — | — | — | — | 40 | 100 | 60 | 45 |
|   | 15.0 | — | — | — | — | 45 | 100 | 65 | 95 |
|   | 30.0 | — | — | — | — | 98 | 100 | 100 | 100 |
|   | 60.0 | — | — | — | — | 100 | 100 | 100 | 100 |
|   | 120.0 | — | — | — | — | 100 | 100 | 100 | 100 |
| 6 | 7.5 | — | — | — | — | 95 | 100 | 85 | 70 |
|   | 15.0 | — | — | — | — | 98 | 100 | 98 | 98 |
|   | 30.0 | — | — | — | — | 100 | 100 | 95 | 98 |
|   | 60.0 | — | — | — | — | 100 | 100 | 100 | 100 |
|   | 120.0 | — | — | — | — | 100 | 100 | 100 | 100 |
|   | 600 | 55 | 100 | 55 | 70 | 100 | 100 | 100 | 100 |
| 7 | 7.5 | — | — | — | — | 55 | 75 | 55 | 25 |
|   | 15.0 | — | — | — | — | 60 | 98 | 90 | 90 |
|   | 30.0 | — | — | — | — | 75 | 100 | 90 | 98 |
|   | 60.0 | — | — | — | — | 98 | 100 | 100 | 100 |
|   | 120.0 | — | — | — | — | 100 | 100 | 100 | 100 |
| 8 | 7.5 | — | — | — | — | 90 | 100 | 60 | 70 |
|   | 15.0 | — | — | — | — | 95 | 100 | 80 | 95 |
|   | 30.0 | — | — | — | — | 95 | 100 | 100 | 100 |
|   | 60.0 | — | — | — | — | 100 | 100 | 100 | 100 |
|   | 120.0 | — | — | — | — | 100 | 100 | 100 | 100 |
| 10 | 7.5 | — | — | — | — | 100 | 100 | 90 | 90 |
|   | 15.0 | — | — | — | — | 100 | 100 | 100 | 98 |
|   | 30.0 | — | — | — | — | 100 | 100 | 100 | 100 |
|   | 60.0 | — | — | — | — | 100 | 100 | 100 | 100 |
|   | 120.0 | — | — | — | — | 100 | 100 | 100 | 100 |
| 15 | 7.5 | — | — | — | — | 100 | 65 | 75 | 70 |
|   | 15.0 | — | — | — | — | 100 | 100 | 98 | 85 |
|   | 30.0 | — | — | — | — | 100 | 100 | 100 | 100 |
|   | 60.0 | — | — | — | — | 100 | 100 | 100 | 100 |
|   | 120.0 | — | — | — | — | 100 | 100 | 100 | 100 |
| 16 | 7.5 | — | — | — | — | 98 | 75 | 75 | 50 |
|   | 15.0 | — | — | — | — | 100 | 98 | 98 | 80 |
|   | 30.0 | — | — | — | — | 100 | 100 | 100 | 100 |
|   | 60.0 | — | — | — | — | 100 | 100 | 100 | 100 |
|   | 120.0 | — | — | — | — | 100 | 100 | 100 | 100 |

TABLE 3-continued

Herbicidal Evaluation

| | | Pre-emergence treatment | | | | Post-emergence treatment | | | |
|---|---|---|---|---|---|---|---|---|---|
| Compound | Dose g a.i./hm² | Zinnia elegans Jacq. | Abutilon theophrasti Medic. | Setaria glauca (L.) Beauv. | Echinochloacrusgalli (L.) Beauv. | Zinnia elegans Jacq. | Abutilon theophrasti Medic. | Setaria glauca (L.) Beauv. | Echinochloacrusgalli (L.) Beauv. |
| 17 | 7.5 | — | — | — | — | 45 | 95 | 55 | 30 |
|  | 15.0 | — | — | — | — | 55 | 98 | 60 | 60 |
|  | 30.0 | — | — | — | — | 65 | 100 | 100 | 100 |
|  | 60.0 | — | — | — | — | 90 | 100 | 100 | 100 |
|  | 120.0 | — | — | — | — | 100 | 100 | 100 | 100 |
|  | 600 | 90 | 90 | 85 | 95 | 100 | 100 | 100 | 100 |
| 22 | 37.5 | 0 | 0 | 0 | 0 | 55 | 30 | 10 | 0 |
|  | 150 | 0 | 0 | 0 | 0 | 90 | 55 | 10 | 5 |
|  | 600 | 0 | 0 | 0 | 0 | 95 | 100 | 15 | 10 |
| 43 | 7.5 | 0 | 100 | 20 | 10 | 98 | 100 | 70 | 10 |
|  | 15 | 25 | 100 | 35 | 60 | 100 | 100 | 80 | 20 |
|  | 37.5 | 50 | 100 | 90 | 90 | 100 | 100 | 25 | 10 |
|  | 150 | 100 | 100 | 98 | 95 | 100 | 100 | 95 | 90 |
|  | 600 | 100 | 100 | 100 | 100 | 100 | 100 | 100 | 100 |
| 45 | 7.5 | 20 | 98 | 70 | 5 | 95 | 98 | 30 | 15 |
|  | 15 | 20 | 100 | 80 | 10 | 100 | 100 | 45 | 15 |
|  | 37.5 | 90 | 95 | 95 | 20 | 100 | 100 | 50 | 25 |
|  | 150 | 95 | 100 | 90 | 85 | 100 | 100 | 85 | 80 |
|  | 600 | 100 | 100 | 100 | 100 | 100 | 100 | 98 | 100 |
| 46 | 7.5 | 40 | 50 | 75 | 10 | 98 | 98 | 45 | 20 |
|  | 15 | 45 | 100 | 60 | 15 | 98 | 100 | 55 | 25 |
|  | 37.5 | 95 | 100 | 95 | 50 | 100 | 100 | 55 | 30 |
|  | 150 | 100 | 100 | 100 | 95 | 100 | 100 | 80 | 75 |
|  | 600 | 100 | 100 | 100 | 100 | 100 | 100 | 100 | 98 |
| 50 | 37.5 | 0 | 0 | 0 | 0 | 98 | 100 | 15 | 10 |
|  | 150 | 30 | 35 | 30 | 10 | 100 | 100 | 65 | 30 |
|  | 600 | 90 | 100 | 90 | 80 | 100 | 100 | 98 | 80 |
| 54 | 37.5 | 0 | 0 | 0 | 0 | 90 | 100 | 35 | 10 |
|  | 150 | 20 | 35 | 20 | 15 | 100 | 100 | 70 | 20 |
|  | 600 | 60 | 90 | 60 | 80 | 100 | 100 | 98 | 75 |
| 55 | 37.5 | 0 | 5 | 0 | 0 | 100 | 100 | 30 | 20 |
|  | 150 | 5 | 20 | 5 | 20 | 100 | 100 | 75 | 35 |
|  | 600 | 80 | 45 | 80 | 40 | 100 | 100 | 90 | 45 |
| 83 | 7.5 | 0 | 0 | 10 | 10 | 65 | 65 | 30 | 25 |
|  | 15 | 10 | 30 | 15 | 10 | 90 | 98 | 45 | 25 |
|  | 37.5 | 50 | 50 | 35 | 25 | 98 | 100 | 50 | 30 |
|  | 150 | 100 | 100 | 80 | 90 | 100 | 100 | 70 | 45 |
|  | 600 | 100 | 100 | 100 | 100 | 100 | 100 | 85 | 90 |
| 88 | 7.5 | 20 | 98 | 65 | 5 | 98 | 98 | 25 | 15 |
|  | 15 | 30 | 100 | 80 | 10 | 100 | 100 | 30 | 20 |
|  | 37.5 | 45 | 85 | 30 | 15 | 100 | 98 | 45 | 25 |
|  | 150 | 100 | 100 | 85 | 80 | 100 | 100 | 70 | 60 |
|  | 600 | 100 | 100 | 100 | 100 | 100 | 100 | 98 | 95 |
| 90 | 37.5 | 5 | 0 | 5 | 0 | 98 | 100 | 25 | 15 |
|  | 150 | 30 | 10 | 20 | 10 | 100 | 100 | 60 | 35 |
|  | 600 | 80 | 30 | 50 | 25 | 100 | 100 | 80 | 40 |
| 284 | 37.5 | 0 | 0 | 0 | 0 | 100 | 95 | 75 | 70 |
|  | 150 | 10 | 50 | 10 | 10 | 100 | 100 | 90 | 80 |
|  | 600 | 35 | 65 | 20 | 20 | 100 | 100 | 100 | 100 |
| 286 | 37.5 | 0 | 0 | 0 | 0 | 85 | 90 | 15 | 20 |
|  | 150 | 0 | 0 | 10 | 5 | 100 | 100 | 70 | 60 |
|  | 600 | 10 | 15 | 30 | 15 | 100 | 100 | 75 | 75 |
| 290 | 37.5 | 0 | 10 | 0 | 0 | 75 | 85 | 40 | 25 |
|  | 150 | 0 | 35 | 10 | 0 | 100 | 98 | 75 | 65 |
|  | 600 | 20 | 60 | 25 | 20 | 100 | 100 | 85 | 70 |
| 396 | 7.5 | — | — | — | — | 30 | 98 | 25 | 20 |
|  | 15.0 | — | — | — | — | 60 | 100 | 55 | 55 |
|  | 30.0 | — | — | — | — | 75 | 100 | 85 | 95 |
|  | 60.0 | — | — | — | — | 100 | 100 | 98 | 100 |
|  | 120.0 | — | — | — | — | 100 | 100 | 100 | 100 |
| 397 | 7.5 | — | — | — | — | 60 | 98 | 55 | 45 |
|  | 15.0 | — | — | — | — | 85 | 100 | 75 | 65 |
|  | 30.0 | — | — | — | — | 95 | 100 | 85 | 100 |
|  | 60.0 | — | — | — | — | 100 | 100 | 100 | 100 |
|  | 120.0 | — | — | — | — | 100 | 100 | 100 | 100 |

TABLE 3-continued

Herbcicidal Evaluation

| | | Pre-emergence treatment | | | | Post-emergence treatment | | | |
|---|---|---|---|---|---|---|---|---|---|
| Compound | Dose g a.i./hm² | Zinnia elegans Jacq. | Abutilon theophrasti Medic. | Setaria glauca (L.) Beauv. | Echinochloacrus-galli (L.) Beauv. | Zinnia elegans Jacq. | Abutilon theophrasti Medic. | Setaria glauca (L.) Beauv. | Echinochloacrus-galli (L.) Beauv. |
| 398 | 7.5 | — | — | — | — | 65 | 98 | 55 | 65 |
| | 15.0 | — | — | — | — | 90 | 98 | 95 | 75 |
| | 30.0 | — | — | — | — | 100 | 100 | 100 | 95 |
| | 60.0 | — | — | — | — | 100 | 100 | 100 | 100 |
| | 120.0 | — | — | — | — | 100 | 100 | 100 | 100 |
| 70% Saflufenacil WG | 7.5 | — | — | — | — | 45 | 100 | 10 | 0 |
| | 15.0 | — | — | — | — | 50 | 100 | 10 | 0 |
| | 30.0 | — | — | — | — | 98 | 100 | 30 | 5 |
| | 60.0 | — | — | — | — | 100 | 100 | 50 | 15 |
| | 120.0 | — | — | — | — | 100 | 100 | 75 | 25 |

70% Saflufenacil WG is commercially available from BASF.
"—" mean no test

Example 19 Crop Safety Study in Greenhouse

Seeds of soybean, cotton, maize, wheat and rice were sown in nutrition soil in paper pot (9 cm diameter), covered with soil in 1 cm and grown in the greenhouse under good growth conditions (temperature, atmospheric humidity, water supply). The compounds of the present invention as emulsifiable concentrate, were applied in pre-emergence and post-emergence treatment by track sprayer (Engineer Research Ltd., pressure 1.95 kg/cm², volume 500 L/hm², track speed 1.48 km/h). Pre-emergence treatment was conducted after seeding 24 hours and post-emergence treatment was done when the respective weeds reached predetermined leaf stage (soybean and cotton at 2- to 4-leaf stage and maize, wheat and rice at 3-leaf stage), the state of growth of the respective crops were visually observed to determine the safety in accordance with the following evaluation standard.

Safety rating scale (%): 0 means no damage to crops; 100 means to kill crops completely.

The results showed that wheat, maize and rice have good safety to compound 43, 45, 46, 83 at 7.5-37.5 g a.i./hm² with pre-emergence and post-emergence application.

Example 20 Weed Spectrum Study in Greenhouse of Compound 6

The method is as example 18.

Example 21 Field Trial

The field trial was conducted in an orchard located at Liaoyang city, Liaoning province, China; the orchard planted mainly apple trees and almond trees, plum trees and pear trees as well, weeding control were conducted three times one year by application of paraquat. Weeds were distributed uniformity and moderate density, mainly of broad-leaf weeds including *Conyza canadensis* (L.)Cronq., *Sonchus brachyotus* DC., *Polygonum aviculare* L., *Humulus scandens* (Lour.) Merr., *Ixeridium sonchifolium* (Maxim.) Shih, *Galium aparine* L. var. *tenerum* Gren. et (Godr.) Rebb., *Rumex japonicus* Houtt. and *Metaplexis japonica* (Thunb.) Makino, partly of grass weed was *Digitaria sanguinalis* (L.) Scop., average height range was between 30 and 40 cm. sprayer was knapsack hand-operated sprayer (AGROLEX HD400) produced by AGROLEx PTE Ltd., spray volume was 675 L/hm², processing date was Jul. 3, 2015. On the 15th day after application, weeds were visually observed to determine the growth inhibition rate (%).

TABLE 4

Weed spectrum of compound 6

| Compound | Dose g a.i./hm² | Cyperus difformis L. (4,5-leaf stage) | Cyperusglomeratus L. (5-leaf stage) | Digitaria sanguinalis (L.) (4,5-leaf stage) | Arthraxon hispidus (Thunb.) Makino (3-leaf stage) | Amaranthus retroflexus L. (height 10-15 cm) |
|---|---|---|---|---|---|---|
| 95% Compound 6 | 7.5 | 30 | 80 | 80 | 60 | 90 |
| | 15 | 60 | 80 | 90 | 85 | 98 |
| | 30 | 90 | 90 | 100 | 90 | 100 |
| | 60 | 95 | 100 | 100 | 100 | 100 |
| | 120 | 100 | 100 | 100 | 100 | 100 |
| 70% Saflufenacil WDG | 7.5 | 5 | 0 | 5 | 15 | 70 |
| | 15 | 5 | 0 | 5 | 20 | 80 |
| | 30 | 10 | 10 | 15 | 30 | 98 |
| | 60 | 15 | 10 | 20 | 35 | 100 |
| | 120 | 70 | 45 | 35 | 45 | 100 |

TABLE 5

| | | Growth inhibition rate (%) of grass weed | Growth inhibition rate (%) of broad-leaf weeds | Total growth inhibition rate (%) of weeds |
|---|---|---|---|---|
| Compound | Dose g a.i./hm$^2$ | | | |
| 95% Compound 6 | 60 | 61.7 | 85.0 | 81.7 |
| | 120 | 71.7 | 93.3 | 91.7 |
| | 180 | 83.3 | 94.3 | 91.7 |
| | 240 | 88.3 | 97.0 | 93.3 |
| | 300 | 94.3 | 92.7 | 98.7 |
| 70% Saflufenacil WDG | 60 | 25.0 | 75.0 | 58.3 |
| 20% Paraquat AS | 375 | 97.7 | 99.3 | 96.7 |

Paraquat: ® gramoxone20% AS (Syngenta)

We claim:

1. Uracil compounds containing isoxazoline ring having general formula (I):

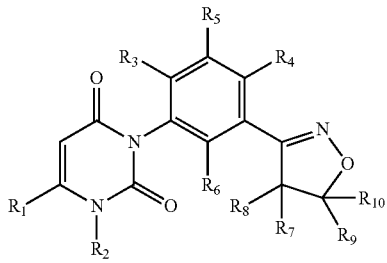

wherein:
$R_1$ is $CF_3$;
$R_2$ is $CH_3$;
$R_3$, $R_4$ are selected from H, F, Cl or $CH_3$;
$R_5$, $R_6$ are H;
$R_7$ is selected from H or $CH_3$;
$R_8$ is selected from H or $CH_3$;
$R_9$ is selected from $CO_2R_1$ or $CH_2OR_{12}$;
$R_{10}$ is selected from H, $CH_3$, $C_2H_5$, or $CHF_2$;
$R_{11}$ is selected from H, $CH_3$, $C_2H_5$, $CH_3CH_2CH_2$, $CH_3CH_2CH_2CH_2$, $(CH_3)_2CH$, $(CH_3)_2CHCH_2$, $(CH_3)_3C$, $CF_3CH_2$, allyl, propargyl, $CH_3OCH_2CH_2$, $C_2H_5OCH_2CH_2$, $CH_3CO_2CH_2CH_2$ or tetrahydrofuranmethyl;
$R_{12}$ is selected from $C_1$-$C_4$alkylcarbonyl, $C_1$-$C_4$haloalkylcarbonyl, $C_3$-$C_6$cycloalkylcarbonyl, $C_1$-$C_4$alkylsulfonyl or $C_1$-$C_4$haloalkylsulfonyl.

2. The compounds according to the claim 1, wherein, in general formula (I):
$R_1$ is $CF_3$;
$R_2$ is $CH_3$;
$R_3$, $R_4$ are selected from H, F or Cl;
$R_5$, $R_6$ are H;
$R_7$ is selected from H or $CH_3$;
$R_8$ is selected from H or $CH_3$;
$R_9$ is selected from $CO_2R_{11}$ or $CH_2OR_{12}$;
$R_{10}$ is selected from H, $CH_3$ or $C_2H_5$;
$R_{11}$ is selected from H, $CH_3$, $C_2H_5$, $CH_3CH_2CH_2$, $CH_3CH_2CH_2CH_2$, $(CH_3)_2CH$, $(CH_3)_2CHCH_2$, $(CH_3)_3C$, $CF_3CH_2$, allyl, propargyl, $CH_3OCH_2CH_2$, $C_2H_5OCH_2CH_2$, $CH_3CO_2CH_2CH_2$ or tetrahydrofuranmethyl;
$R_{12}$ is selected from $C_1$-$C_4$alkylcarbonyl, $C_1$-$C_4$haloalkylcarbonyl, $C_3$-$C_6$cycloalkylcarbonyl, $C_1$-$C_2$alkylsulfonyl or $C_1$-$C_2$haloalkylsulfonyl.

3. The compounds according to the claim 2, wherein, in general formula (I):
$R_1$ is $CF_3$;
$R_2$ is $CH_3$;
$R_3$, $R_4$ are selected from H, F or Cl;
$R_5$, $R_6$ $R_7$, $R_8$ are H;
$R_9$ is selected from $CO_2R_{11}$ or $CH_2OR_{12}$;
$R_{10}$ is selected from H, $CH_3$ or $C_2H_5$;
$R_{11}$ is selected from H, $CH_3$, $C_2H_5$, $CH_3CH_2CH_2$, $CH_3CH_2CH_2CH_2$, $(CH_3)_2CH$, $(CH_3)_2CHCH_2$, $(CH_3)_3C$, $CF_3CH_2$, allyl, propargyl, $CH_3OCH_2CH_2$, $C_2H_5OCH_2CH_2$, $CH_3CO_2CH_2CH_2$ or tetrahydrofuranmethyl;
$R_{12}$ is selected from $C_1$-$C_4$alkylcarbonyl, cyclopropylcarbonyl or $C_1$-$C_2$alkylsulfonyl.

4. A method of controlling weeds comprising applying the compound having general formula (I) according to claim 1 to a plant.

5. A herbicidal composition comprising the compound having general formula (I) of claim 1 as an active ingredient, wherein the weight percentage of the active ingredient in the composition is from 0.1-99%.

6. A method of controlling weeds comprising applying a herbicidal composition according to claim 5 to a plant.

* * * * *

UNITED STATES PATENT AND TRADEMARK OFFICE
CERTIFICATE OF CORRECTION

PATENT NO. : 10,550,111 B2
APPLICATION NO. : 15/527864
DATED : February 4, 2020
INVENTOR(S) : Changling Liu et al.

It is certified that error appears in the above-identified patent and that said Letters Patent is hereby corrected as shown below:

In the Claims

Claim 1, (Column 51, Line 45) should read:
-- $R_9$ is selected from $CO_2R_{11}$ or $CH_2OR_{12}$; --

Signed and Sealed this
Nineteenth Day of April, 2022

Katherine Kelly Vidal
*Director of the United States Patent and Trademark Office*